US006706290B1

(12) United States Patent
Kajander et al.

(10) Patent No.: US 6,706,290 B1
(45) Date of Patent: Mar. 16, 2004

(54) METHODS FOR ERADICATION OF NANOBACTERIA

(76) Inventors: Olvai E. Kajander, P.O. B. 1627, FIN-70211 Kuopio (FI); Neva Ciftcioglu, P.O. B. 1627, FIN-70211 Kuopio (FI)

( * ) Notice: Subject to any disclaimer, the term of this patent is extended or adjusted under 35 U.S.C. 154(b) by 0 days.

(21) Appl. No.: 09/347,189

(22) Filed: Jul. 2, 1999

Related U.S. Application Data

(60) Provisional application No. 60/091,716, filed on Jul. 6, 1998.

(51) Int. Cl.$^7$ .................. A01N 41/00; A01N 31/00; A01N 33/12; A01N 35/00; A01N 37/00; A01N 59/00; A61K 31/00; A61L 2/00

(52) U.S. Cl. .................. 424/616; 422/1; 422/22; 422/24; 422/26; 422/27; 422/28; 422/36; 424/666; 424/DIG. 6; 432/9; 514/36; 514/37; 514/39; 514/41; 514/141; 514/152; 514/159; 514/165; 514/166; 514/192; 514/198; 514/256; 514/390; 514/392; 514/472; 514/474; 514/553; 514/557; 514/561; 514/574; 514/576; 514/634; 514/643; 514/693; 514/694; 514/705; 514/709; 514/716; 514/718; 514/724; 514/738

(58) Field of Search .................. 424/409, 666, 424/DIG. 6, 613; 514/557, 588, 693, 694, 724, 36, 37, 39, 41, 141, 152, 159, 165, 166, 192, 198, 256, 390, 392, 472, 474, 553, 561, 574, 576, 634, 643, 705, 709, 716, 718, 738; 422/1, 22, 24, 26, 27, 28, 36; 432/9

(56) References Cited

U.S. PATENT DOCUMENTS

| 3,683,080 A | 8/1972 | Francis |
| 4,845,125 A | 7/1989 | Geier |
| 5,135,851 A | 8/1992 | Kajander |
| 5,183,815 A | 2/1993 | Saari et al. |
| 5,900,410 A | 5/1999 | Hartmann |

FOREIGN PATENT DOCUMENTS

| DE | 31 27 270 | 3/1983 |
| EP | 0 270 254 | 6/1988 |
| EP | 0 460 414 | 11/1991 |
| EP | 0 702 963 | 3/1996 |
| GB | 1 106 166 | 3/1968 |
| GB | 2 164 851 | 4/1986 |
| WO | 90/00201 | 1/1990 |
| WO | 96/07408 | 3/1996 |

OTHER PUBLICATIONS

Wainwright, "Nanobacteria and associated 'elementary bodies' in human disease and cancer", Microbiology (1999), vol. 145, pp. 2623, 2624.*
Abbot, "Battle lines drawn between 'nanobacteria' researchers", Nature (1999), vol. 401, p. 105.*
Kajander et al., "Nanobacteria: An Alternative Mechanism for Pathogenic Intra– and Extracellular Calcification and Stone Formation", PNAS, 1998, pp. 8274–8279, vol. 95, No. 14, National Academy of Sciences, Washington, D.C., USA.
Ciftcioglu et al, "Nanobacteria: An Infectious Cause for Kidney Stone Formation", *Kidney International*, vol. 56 (1999), pp. 1893–1898.
Kajander et al, "Nanobacteria: An Alternative Mechanism for Pathogenic Intra– and Extracellular Calcification and Stone Formation", *Proc. Natl. Acad. Sci. USA*, vol. 95, pp. 1–6, (Jun. 1998).
Vali et al, "Nanoforms: A New Type of Protein–Associated Mineralization", *Gerochimica et Cosmochimica Acta*, vol. 65, No. 1, pp. 63–74 (2001).
Kajander et al, "Nanobacteria: Controversial Pathogens in Nephrolithiasis and Polycystic Kidney Disease", *Current Opinon in Nephrology and Hypertension* (2001) vol. 10, pp. 445–452.
Ciftcioglu et al, "Interaction of Nanobacteria with Cultured Mammalian Cells", *Pathophysiology*, vol. 4 (1998) pp. 259–270.
Kajander et al, "Comparison of Staphylococci and Novel Bacteria–Like Particles from Blood", Mollby, Flock, Nord, and Christensson (Eds.), *Staphylococci and Staphylococcal infections, Proceedings of the 7$^{th}$* International Symposium, Stockholm, Jun. 29–Jul. 3, 1992, Zbl. Bakt. Supl. 26. (1994) pp. 147–149.
Akerman et al, "Scanning Electron Microscopy of Nanobacteria—Novel Biofilm Producing Organisms in Blood", *Scanning* vol. 15, Supplement III (1993).
Ciftcioglu et al, "Extraordinary Growth Phases of Nanobacteria Isolated From Mammalian Blood", Proceedings Reprint, *Reprinted from Instruments, Methods, and Missions for the Investigation of Extraterrestrial Microorganisms*, Jul. 29–Aug. 1, 1997 PIE The International Society for Optical Engineering 1997, vol. 3111, pp. 429–435.
Ciftcioglu et al, "A New Potential Threat in Antigen and Antibody Products: Nanobacteria", *Vaccines97* (May 1997), pp. 99–103.

(List continued on next page.)

*Primary Examiner*—Thurman K. Page
*Assistant Examiner*—Frank Choi
(74) *Attorney, Agent, or Firm*—Burns, Doane, Swecker & Mathis, L.L.P.

(57) ABSTRACT

Nanobacteria contribute to pathological calcification in the human and animal body, including diseases such as kidney stones, salivary gland stones, dental pulp stones and atherosclerosis. The present invention provides methods for sterilizing articles contaminated with nanobacteria. The present invention also provides methods of treating patients infected with nanobacteria. In particular, the present invention provides a method for preventing the recurrence of kidney stones in a patient that has suffered from kidney stones, comprising administration of an antibiotic, a bisphosphonate, or a calcium chelator, either alone or in combination, in an amount effective to inhibit or prevent the growth and development of nanobacteria.

22 Claims, 27 Drawing Sheets

OTHER PUBLICATIONS

Neva çiftçioglu et al., "A New Potential Threat in Antigen and Antibody Products: Nanobacteria" *Vaccines 97*, Cold Spring Harbor Laboratory Press 1997, pp. 99–103.

E.O. Kajander et al., "Comparison of Staphylococci and Novel Bacteria–Like Particles from Blood", Staphylococci and Staphylococcal Infections, Proceedings of the 7th International Symposium, Stockholm, Jun. 29–Jul. 3, 1991, Zbl. Bakt. Supp. 256, pp. 147–149 (1994).

K.K. Akerman et al., "Radiolabeling and in vivo Distribution of Nanobacteria in Rabbit", *SPIE–The International Society for Optical Engineering*, vol. 3111, pp. 436–442 (1997).

E. Olavi Kajander et al., "Mineralization by Nanobacteria", *SPIE–The International Society for Optical Engineering*, vol. 3441, pp. 86–94 (1998).

Neva çiftçioglu et al., "Sedimentary Rocks in Our Mouth: Dental Pulp Stones Made by Nanobacteria", *SPIE–The International Society for Optical Engineering*, vol. 3441, pp. 130–136 (1998).

Neva çiftçioglu et al., "Interaction of Nanobacteria With Cultured Mammalian Cells", *Pathophysiology* 4:259–270 (1998).

E. Olavi Kajander et al., "Nanobacteria: an Alternative Mechanism for Pathogenic Intra– and Extracellular Calcification and Stone Formation", *Proc. Natl. Acad. Sci. USA* 95:000–000 (6 pages) (1998).

M. Björklund et al., "Extraordinary Survival of Nanobacteria Under Extreme Conditions",*SPIE–The International Society for Optical Engineering*, vol. 3441, pp. 123–129 (1998).

Neva çiftçioglu et al., "Stone Formation and Calcification by Nanobacteria in Human Body", *SPIE–The International Society for Optical Engineering*, vol. 3441, pp. 105–111 (1998).

"Policy of the Journal and Instructions to Authors for 1991 Policy and Organization of the Journal", *Biochem. J.*, (1991) 273, p. 8, Portalnd Press, London, Great Britain.

"Weight/Volume Percent", 1998, http://dl.clackamas.c-c.or.us/ch105–05/wtvolpct.htm.

Chemical Abstracts, vol. 127, No. 16, Oct. 20, 1997.

Chemical Abstracts, vol. 102, No. 13, Apr. 1, 1985.

Chemical Abstracts, vol. 125, No. 19, Nov. 4, 1996.

Kajander, Proc. Natl. Acad. Sci. USA (1998), 95(14), S. 8274–8279.

Vogel, Science 281, p. 158, Jul. 10, 1998.

* cited by examiner

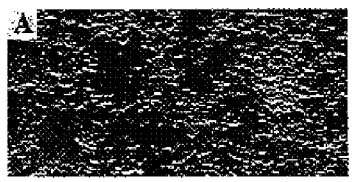
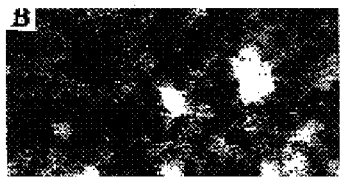
FIG. 1A     FIG. 1B     FIG. 1C
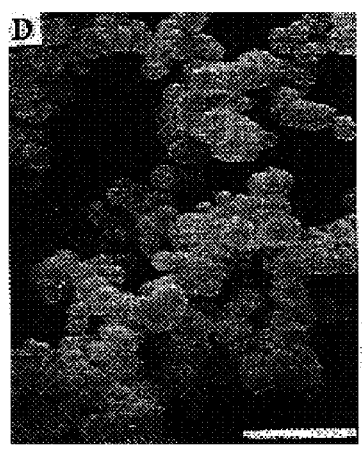
FIG. 1D     FIG. 1E     FIG. 1F
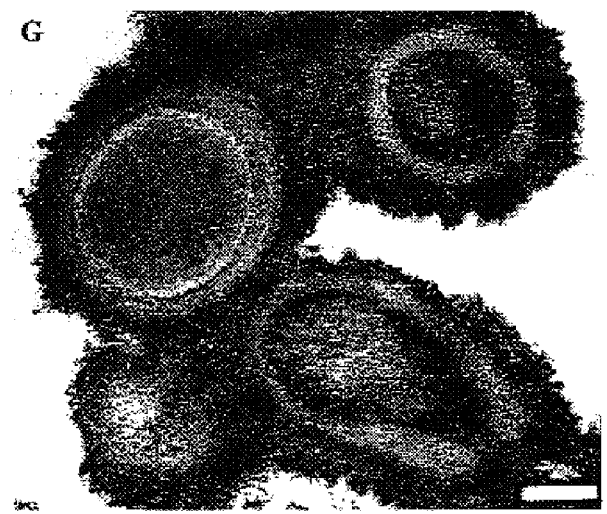
FIG. 1G

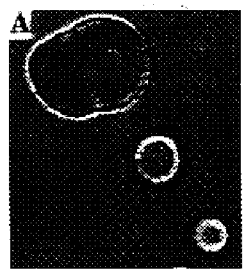 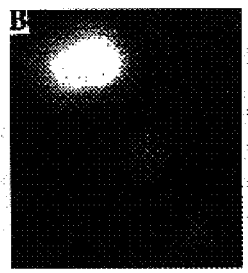 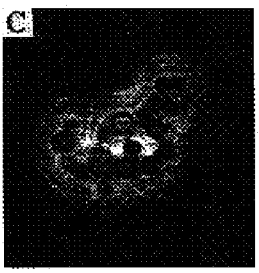 
FIG. 3A   FIG. 3B   FIG. 3C   FIG. 3D
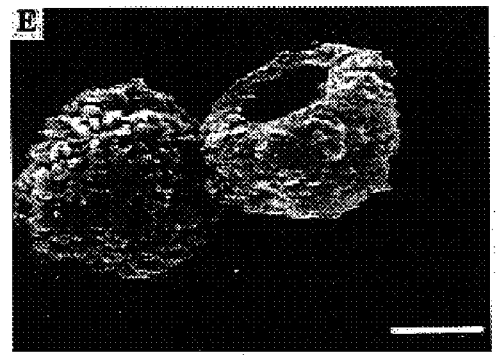 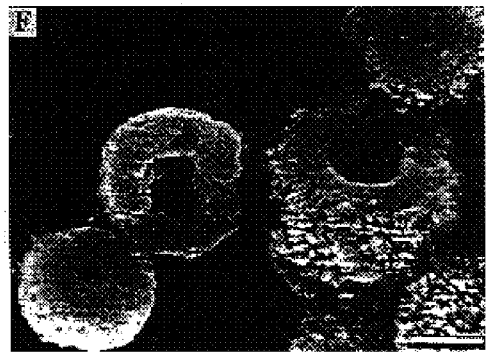
FIG. 3E   FIG. 3F
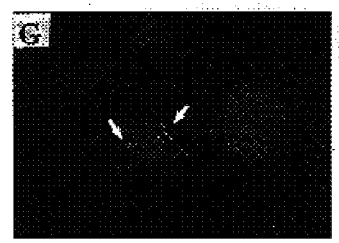 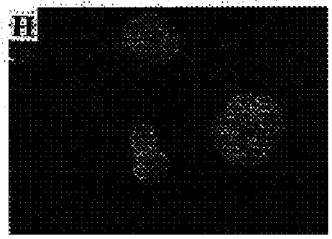 
FIG. 3G   FIG. 3H   FIG. 3I
  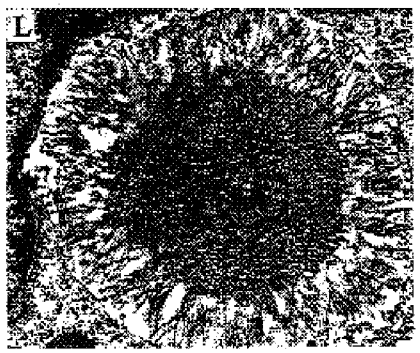
FIG. 3J   FIG. 3K   FIG. 3L

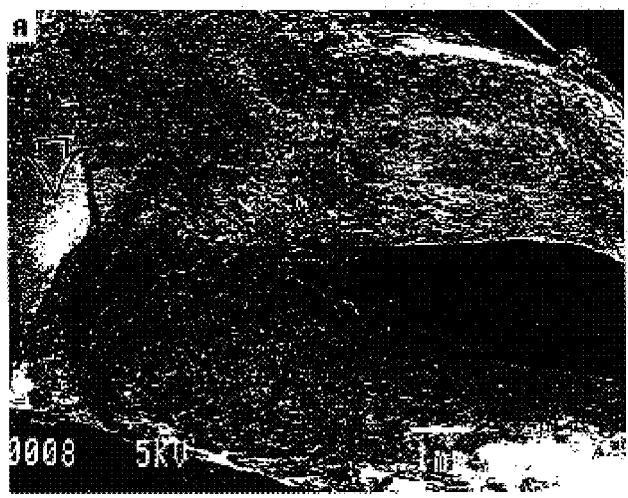 
FIG. 8A　　　　　　　　FIG. 8B
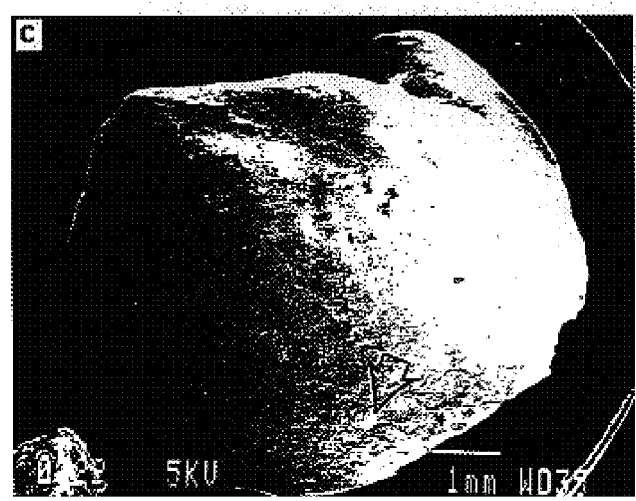 
FIG. 8C　　　　　　　　FIG. 8D

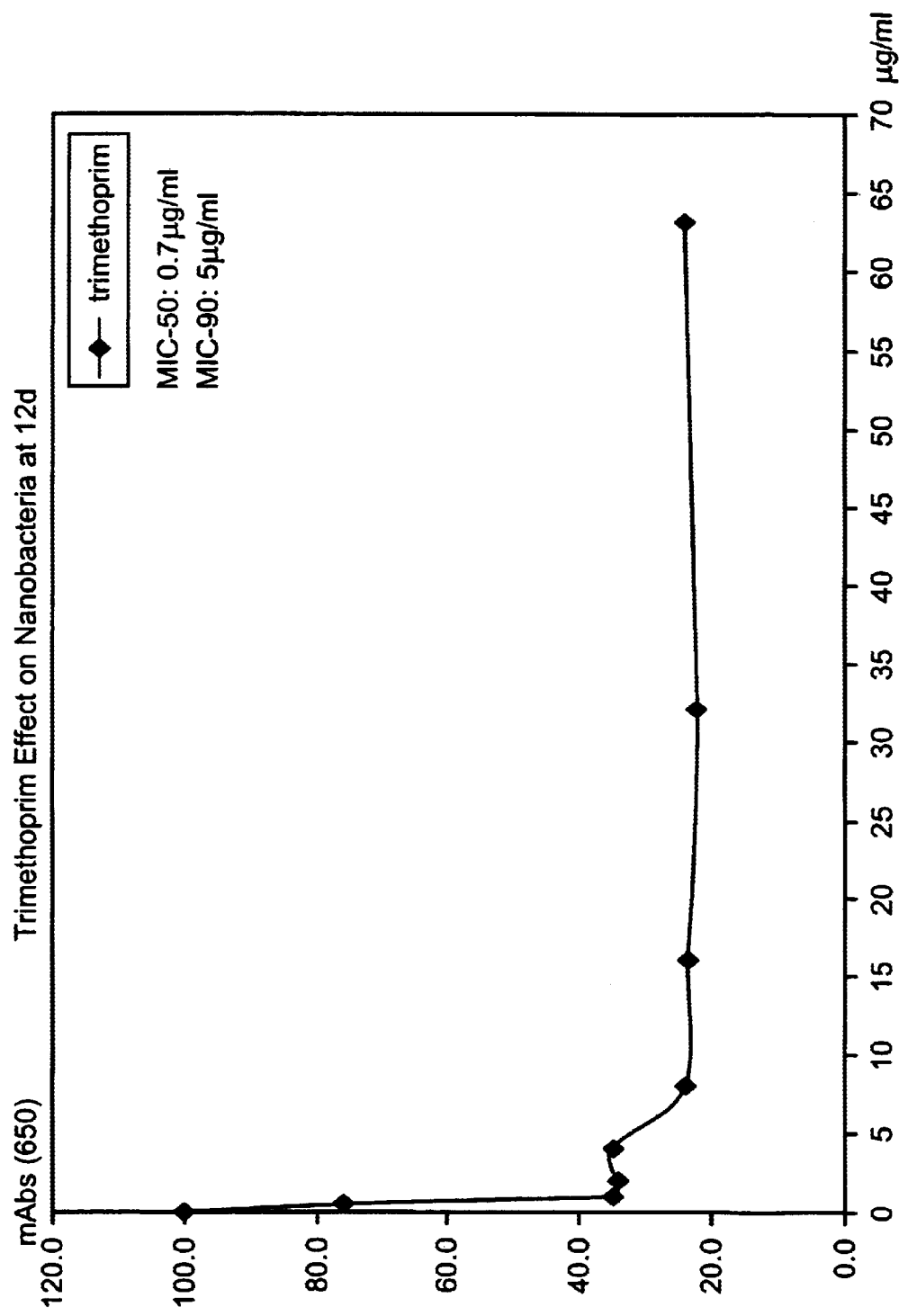

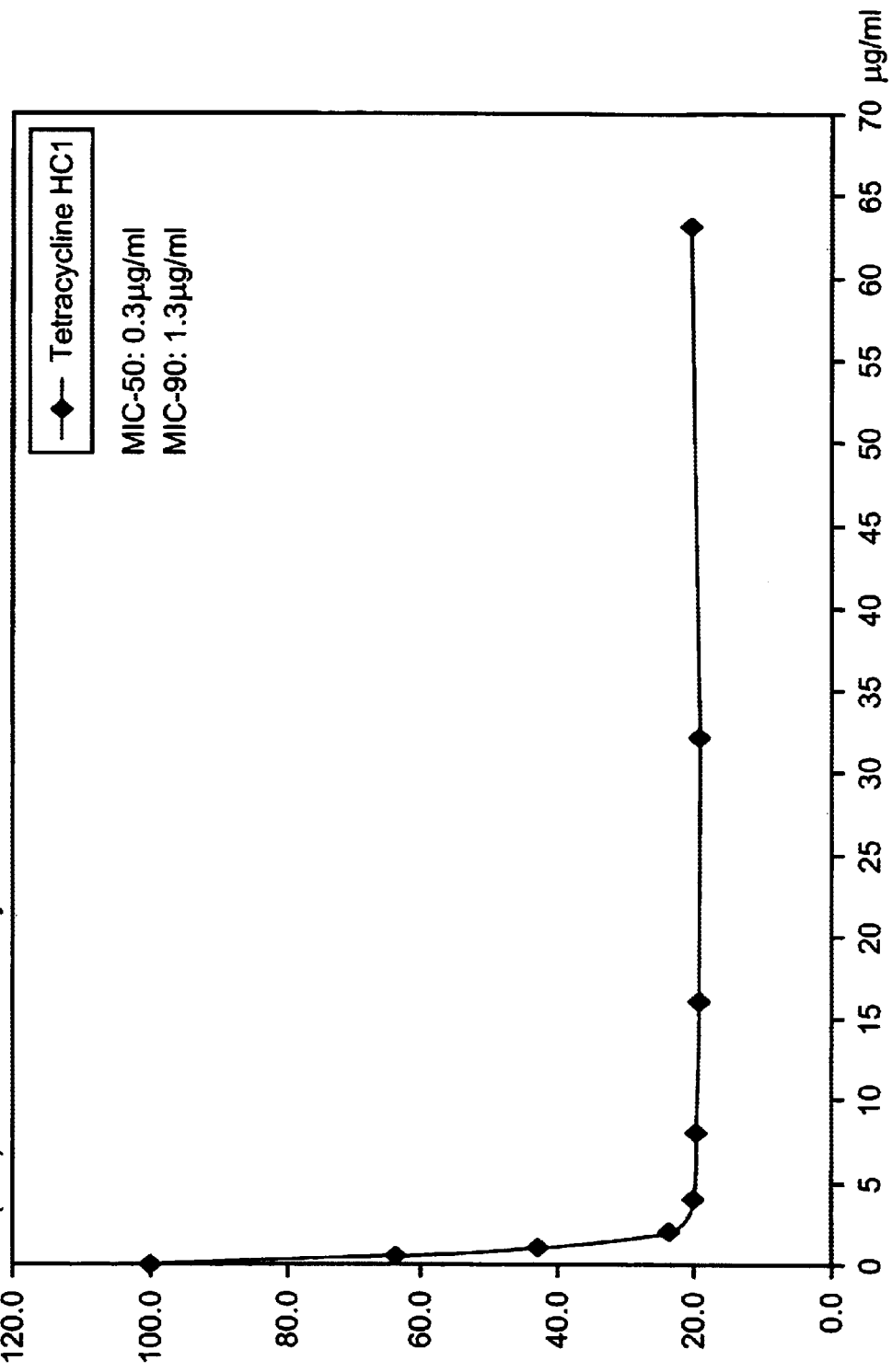

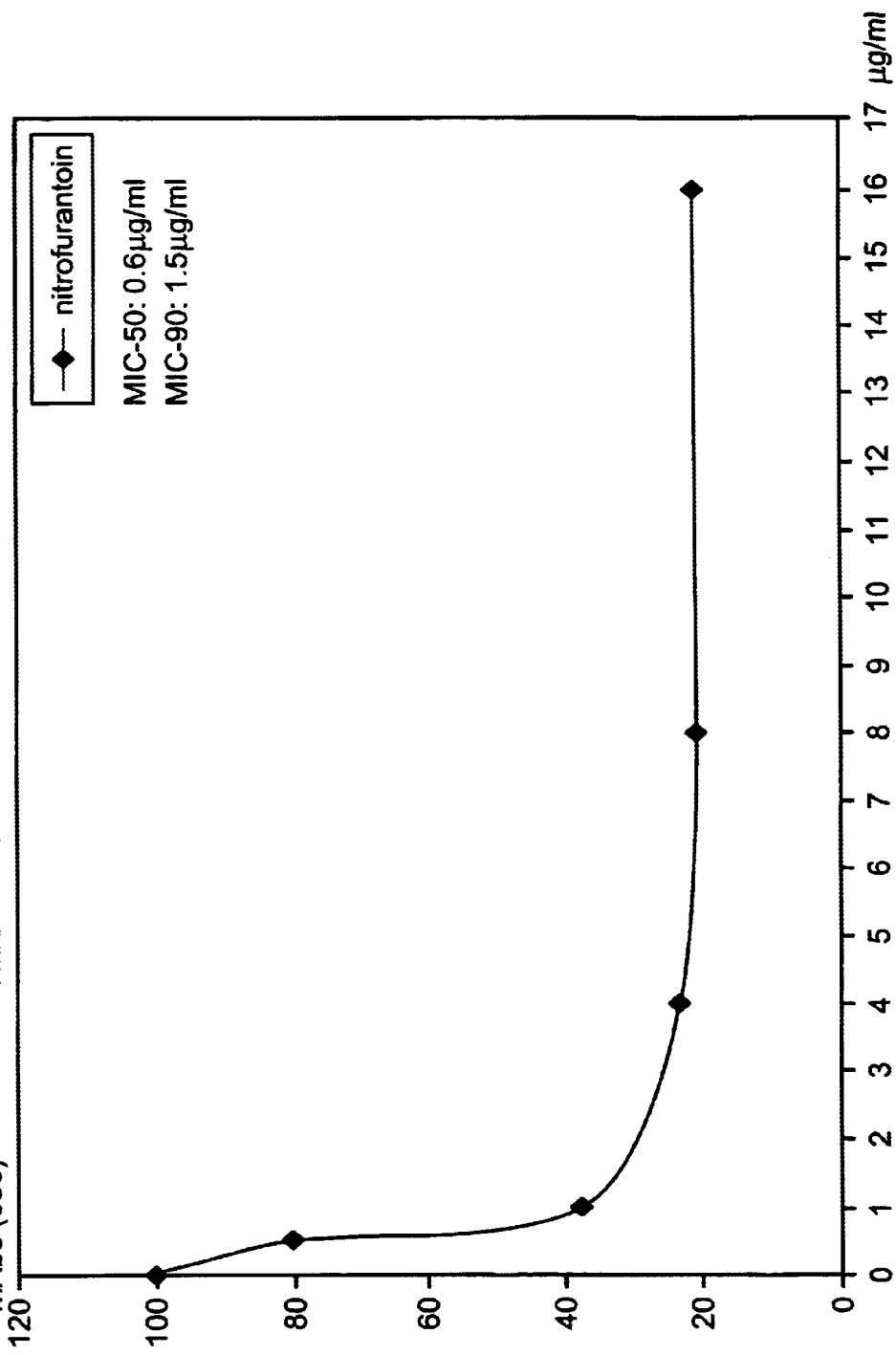

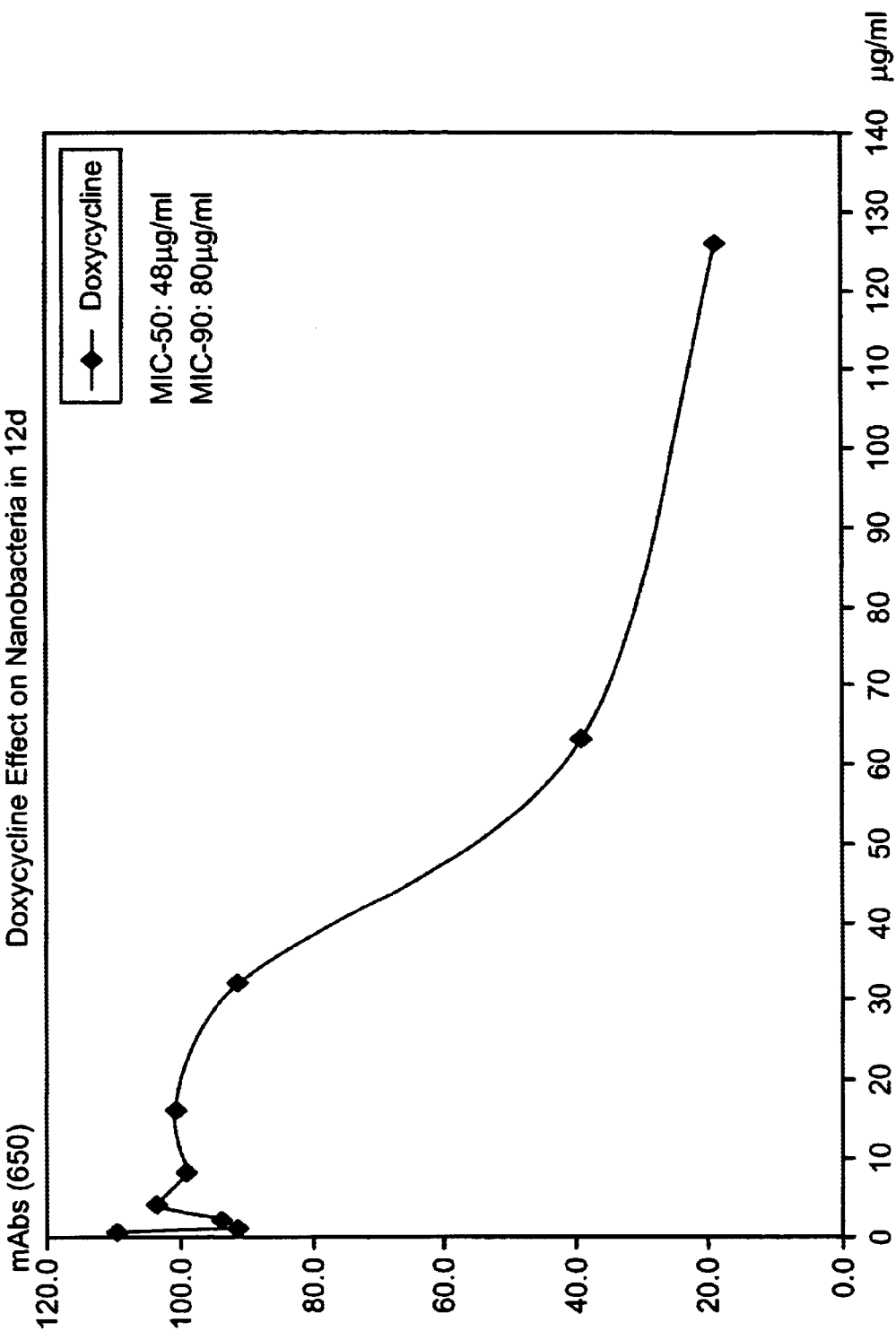

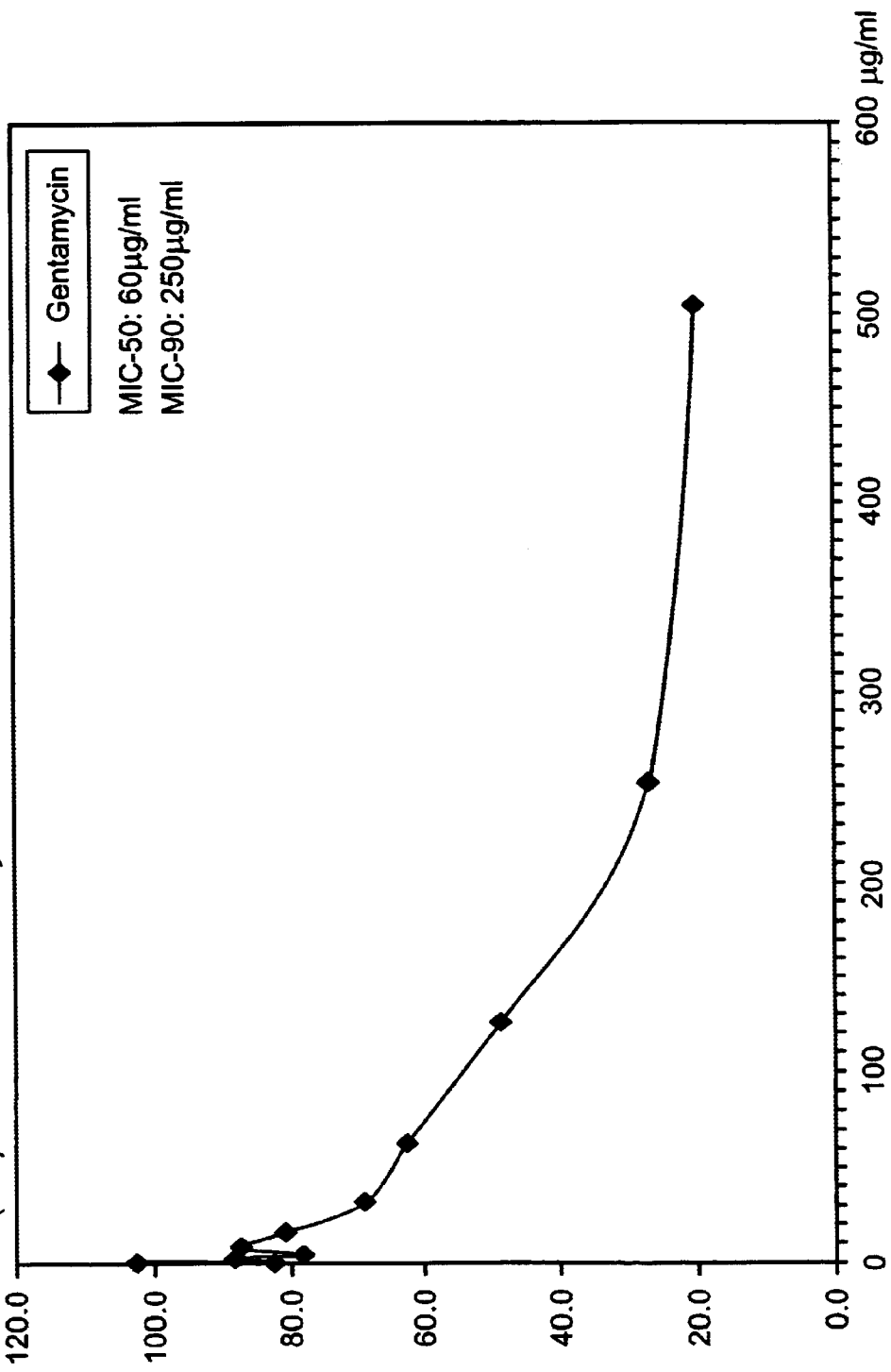

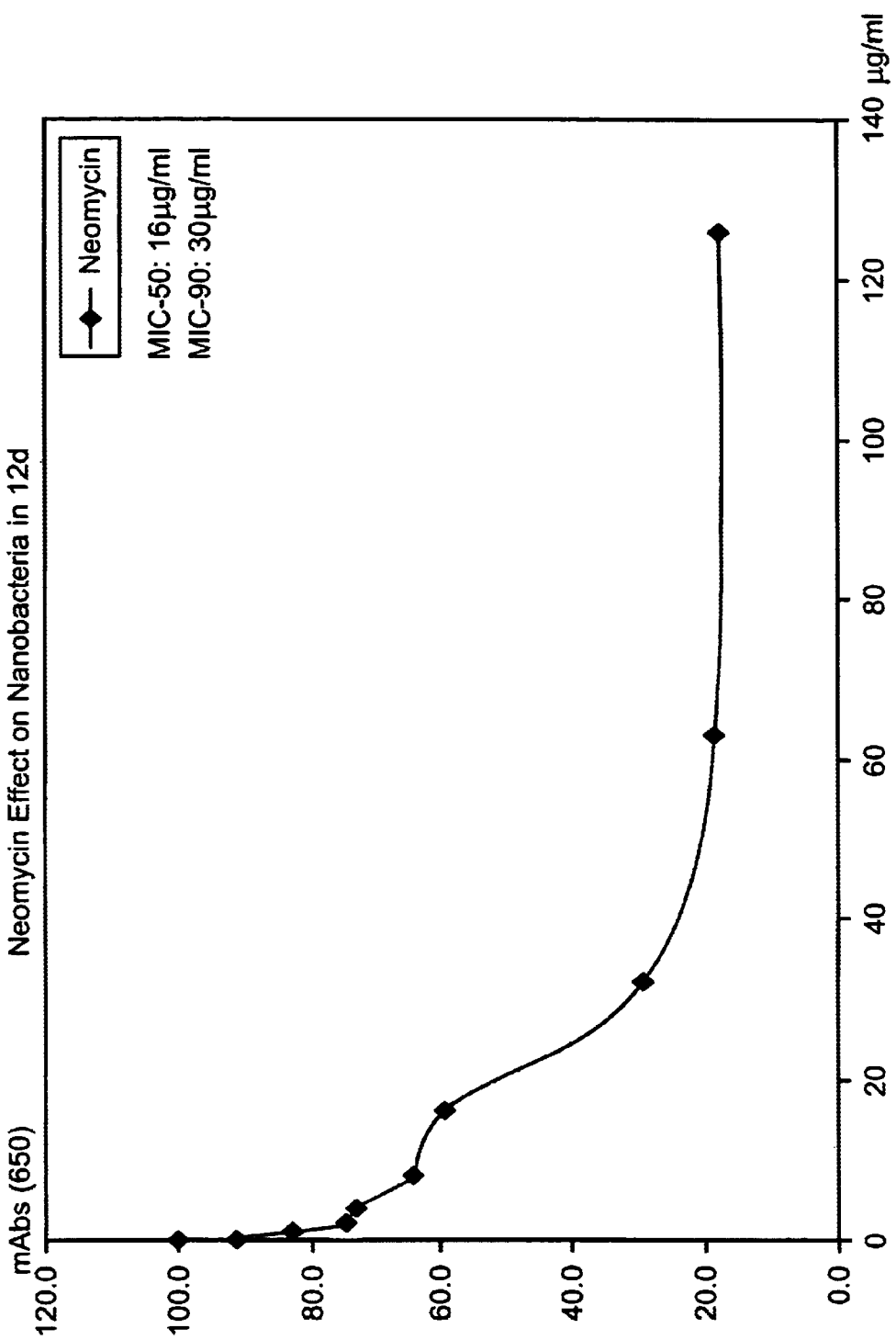

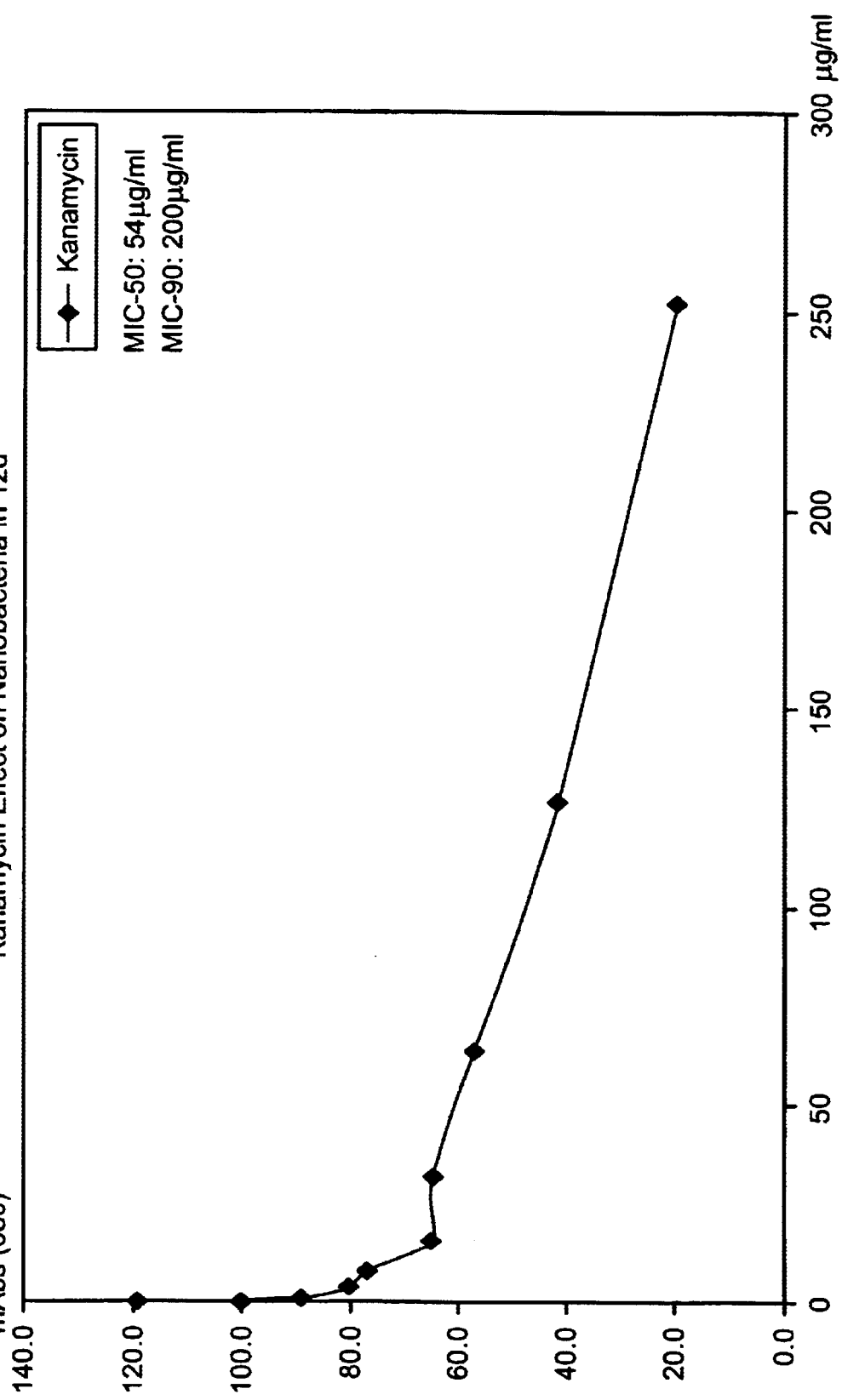

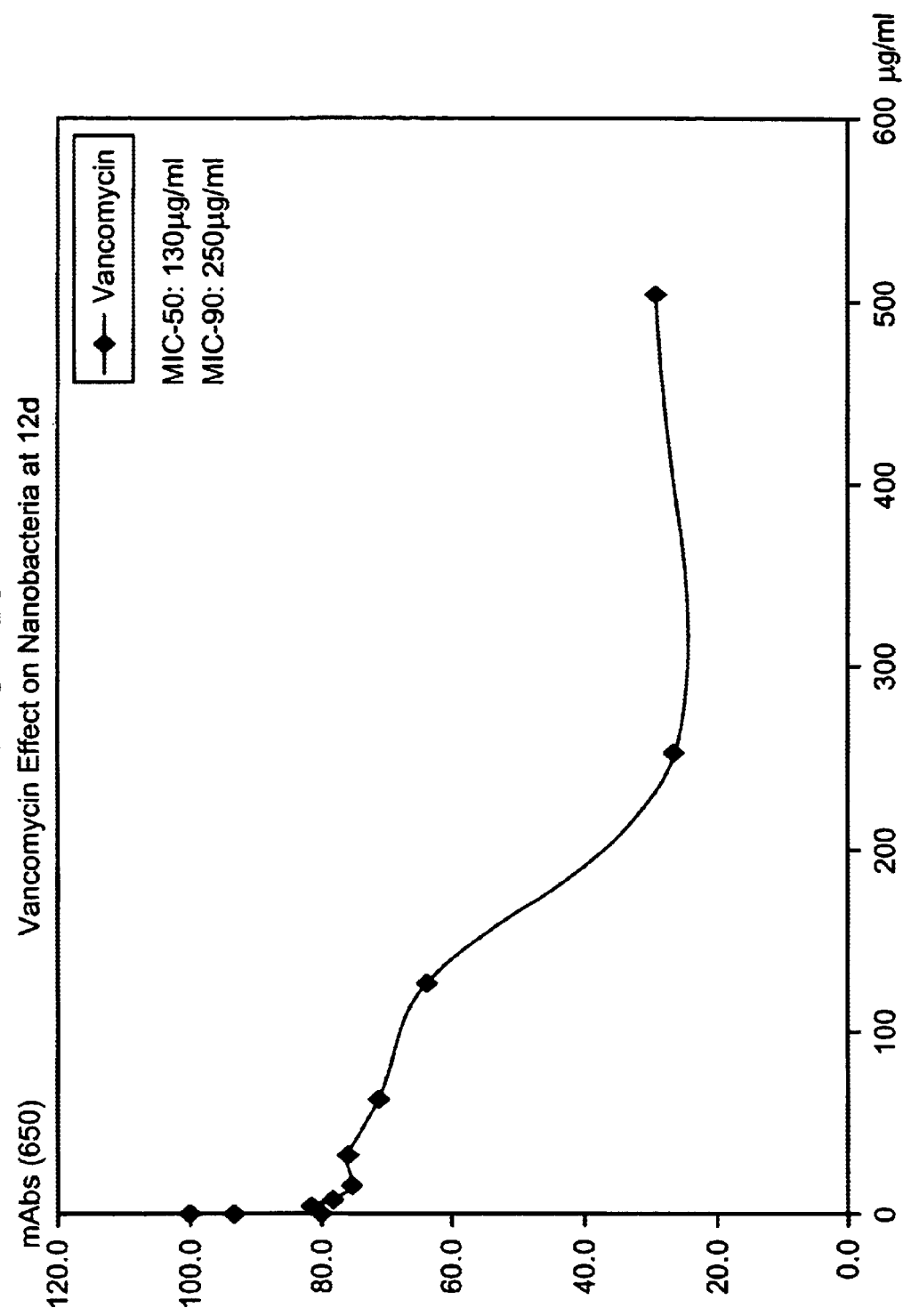

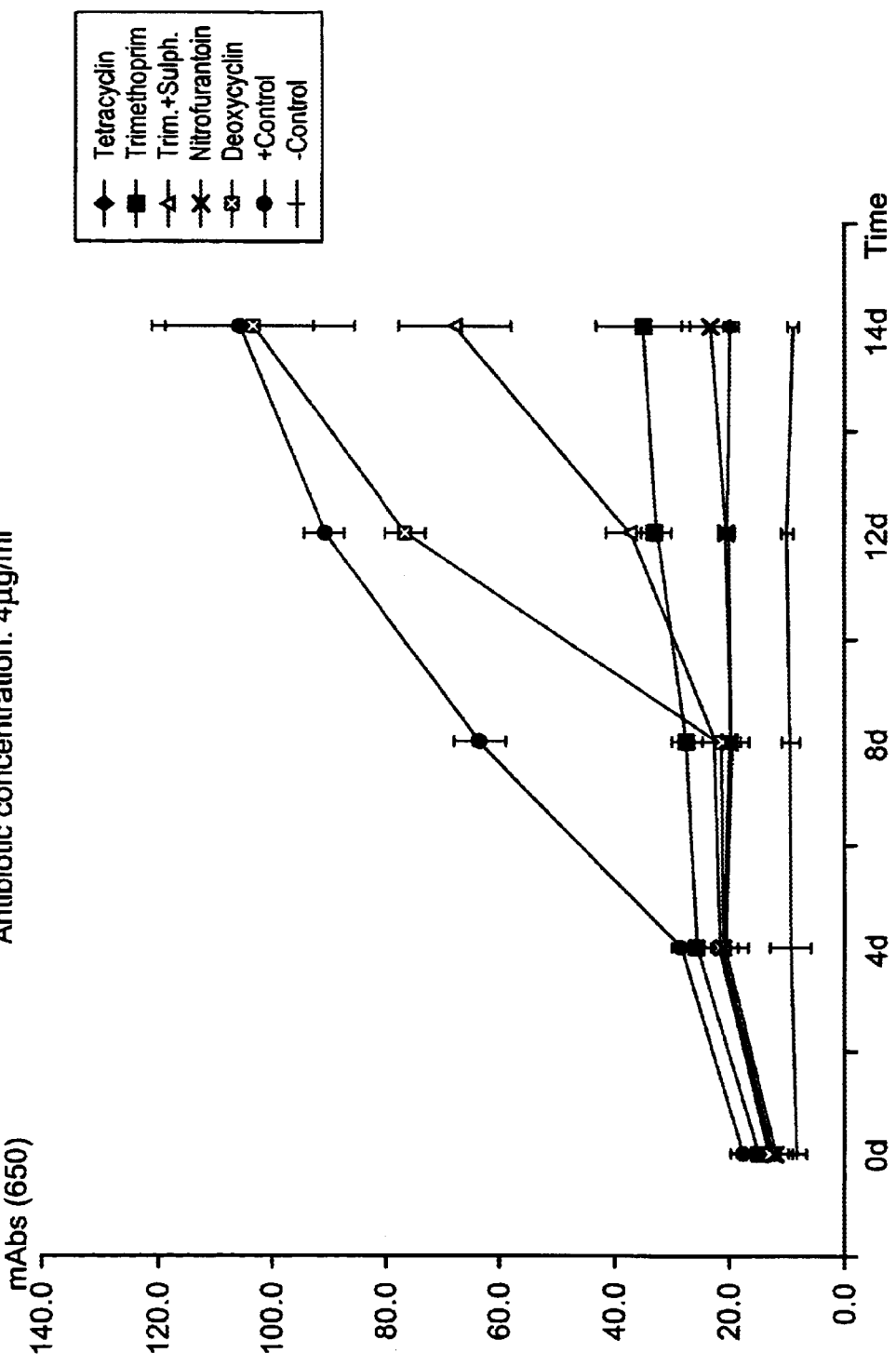

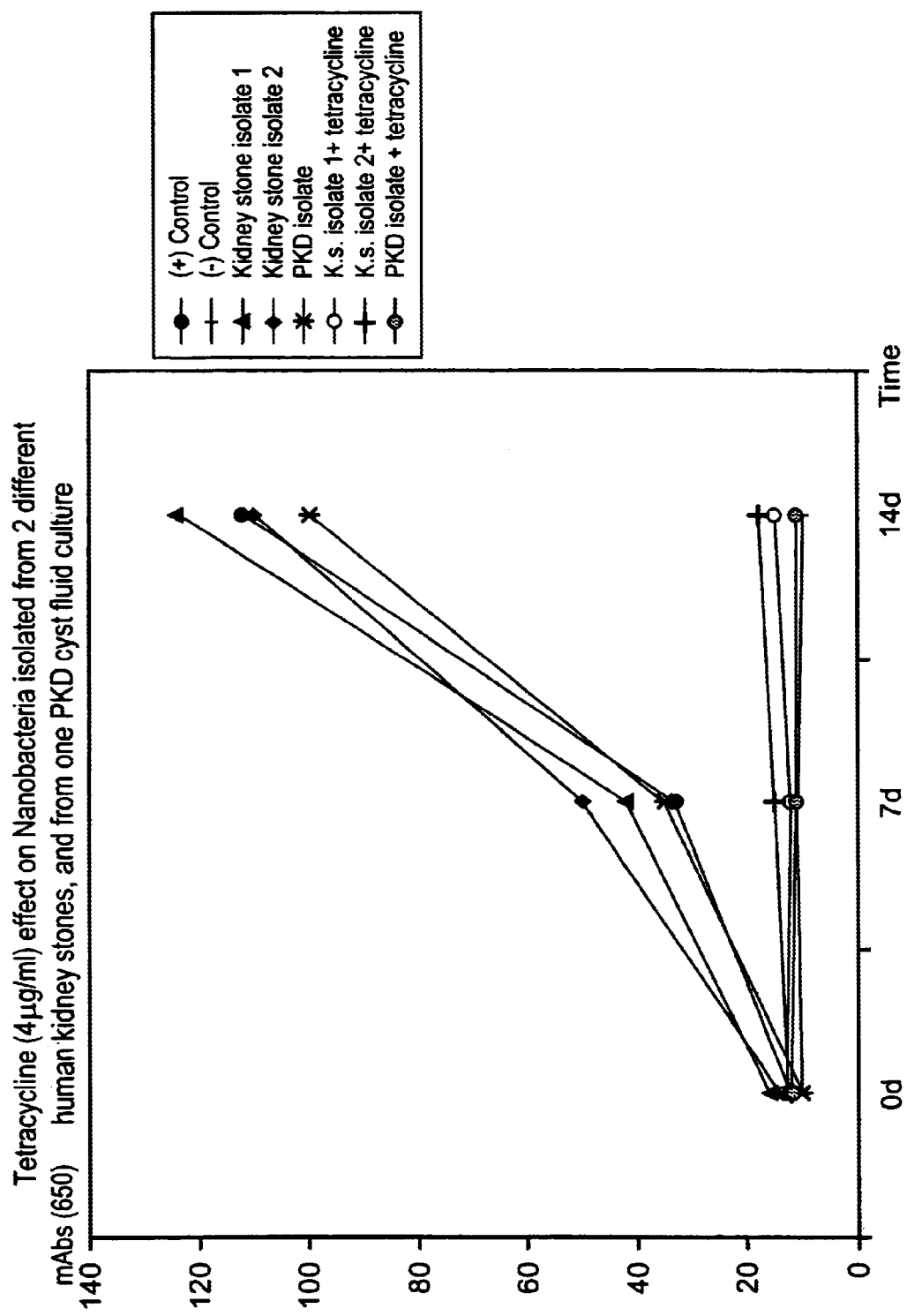

METHODS FOR ERADICATION OF NANOBACTERIA

This application claims the benefit of Provisional Application No. 60/091,716, filed Jul. 6, 1998.

BACKGROUND OF THE INVENTION

1. Field of the Invention

The present invention relates to methods of disinfecting articles infected with nanobacteria, and methods of treating patients infected with nanobacteria.

2. Description of the Related Art

The formation of discrete and organized inorganic crystalline structures within macromolecular extracellular matrices is a widespread biological phenomenon generally referred to as biomineralization. Mammalian bone and dental enamel are examples of biomineralization involving apatite minerals. Environmental apatite stones have almost the same chemical composition as in bone and dentine. Recently, bacteria have been implicated as factors in biogeochemical cycles for mineral formation in aqueous sediments. The principal constituent of modern authigenic phosphate minerals in marine sediments is carbonate (hydroxy) fluorapatite $Ca_{10}(PO_4)_{6-x}(CO_3)_x(F,OH)_{2+x}$. Microorganisms are capable of depositing apatite outside thermodynamic equilibrium in sea water. They can segregate Ca from Mg, and actively nucleate carbonate apatite by means of specific oligopeptides under conditions pH <8.5 and [Mg]:[Ca]>0.1. Such conditions are also present in the human body.

Nanobacteria approach the theoretical limit of the self-replicating life with a size of only one hundredth of that of usual bacteria. Nanobacteria can be isolated from mammalian blood and blood products (see, U.S. Pat. No. 5,135,851 to Kajander, the contents of which are incorporated herein by reference). Energy-dispersive X-ray microanalysis and chemical analysis reveals that nanobacteria produce biogenic apatite on their cell envelope. The thickness of the apatite depends mostly on the culture conditions of the nanobacteria. Nanobacteria are the smallest cell walled, apatite forming bacteria isolated from mammalian blood and blood products. Their small size (0.05–0.5 μm), and unique properties make their detection difficult with conventional microbiological methods. In nanobacteria-infected mammalian cells, electron microscopy revealed intra- and extracellular acicular crystal deposits, stainable with von Kossa staining and resembling calcospherules found in pathological calcification.

The present inventors have discovered nanobacteria in human and cow blood that are cytotoxic in vitro and in vivo. They have been deposited in DSM, Braunschweig, Germany at accession No. 5819–5821. Human and bovine nanobacteria grow similarly, share the same surface antigens, and other special features. They both produce carbonate apatite as well. Nanobacteria possess unusual properties making their detection difficult with standard microbiological methods. Although they typically have diameters of 0.2–0.5 μm, they also exist in tiny forms (0.05–0.2 μm) as observed using transmission electron microscopy (TEM). Thus nanobacteria manage to pass through 0.1 μm filters. Nanobacteria are poorly disruptable, stainable, fixable and exceptionally resistant to heat. Their doubling time is about 3 days. High doses of γ-irradiation or aminoglycoside antibiotics prevented their multiplication. According to the 16S rRNA gene sequence (EMBL X98418 and X98419), nanobacteria fall within the α-2 subgroup of Proteobacteria, which also includes Brucella and Bartonella species. The latter genera include human and animal pathogens that share similarities with nanobacteria, e.g., some of the same antigens and cytopathic effects.

Competition for nutrients necessary for life is enormous in natural environments and thus clever adaptations and survival strategies for unfavorable conditions are needed. Bacteria can form spores, cysts and biofilm, which help them survive unfavorable periods of time. Bacteria in such forms have significantly slower metabolic functions, but vegetative cells can slow down their metabolism as well. The increased resistance of bacteria in biofilm or as spores is not only because of the slower metabolic rate. The impermeable structures around the organism serve as mechanical barriers blocking the entrance of potentially harmful compounds. Some additional mechanisms are also known which help in the survival of bacteria. The heat resistance of bacterial spores can be attributed to three main factors, these are protoplast dehydration, mineralization and thermal adaptation. Radiation resistance is commonly associated with sophisticated DNA repair systems. Minimizing metabolic rate and multiplication are obviously the main preconditions for bacterial survival, allowing time for the repair of DNA and other damaged cellular components. Very slow metabolism, and ability to form biofilm are also characteristics of nanobacteria. Because of their minimal size, the presence of complicated systems for nucleic acid repair in nanobacteria seems very unlikely. A possible explanation for the observed gamma irradiation resistance may be their very small size, and the peculiarities in their nucleic acid structure.

Apatite may play a key role in the formation of kidney stones. The crystalline components of urinary tract stones are calcium oxalate, calcium phosphate, struvite, purines, or cystine. The majority of urinary stones are admixtures of two or more components, with the primary admixture being calcium oxalate and apatite. Furthermore, fermentor model studies have shown that calcium phosphate nidi are always formed initially, and may subsequently become coated with calcium oxalate or other components. Urinary tract infection, causing struvite and carbonate apatite formation, is a common cause of kidney stones. Conventional therapy has usually consisted of surgical removal of the stone, combined with a short course of antimicrobial therapy. Such treatment is curative in about 50% of cases. Recurrent stone formation and progressive pyelonephritis occur in those who are not cured. The morbidity and expense that result from this disease is significant.

Tissue calcification of carbonate apatite in nature is common in other diseases, e.g., atherosclerotic plaques accumulate calcium phosphate. 25% of atherosclerotic plaques in human aorta specimens were found to contain nanobacterial by immunoassay and immunohistochemical staining. Hemodialysis patients can develop extensive metastatic and tumoral calcification. Acute periarthritis is apatite arthropathy related to intratendinous calcifications. Apatite crystals also cause inflammation when injected into the synovial space. Tissue calcification is also found in several kinds of cancer.

Pulp stones or denticles are polymorphous mineralized bodies of various sizes occasionally found in the pulpal connective tissue of human teeth. Their etiology remains unclear although they have been frequently associated with aging or pathology of the pulp. They may also be present in permanent teeth that are impacted free of pathology for a long time. Although pulp stones have been extensively studied morphologically, their origin is still obscure and little is known about their chemical composition. An histochemical study of pulpal calcifications has shown that the organic matrix consists of reticular connective tissue fibers and a ground substance containing glycoproteins and acid polysaccharides. The mineral phase of pulp calcification has been studied with X-ray energy dispersive spectrometry and chemical analysis, and proven that calcium salts are deposited in the form of apatite, possibly carbonate containing apatite. In fact, there is not much difference between the chemical structure of a tooth and denticles. Bone and tooth formation in the body have similar mechanisms, leaving many unanswered questions. Apatite formation in the body (except in tooth and bone) is called pathologic biomineralization, e.g., dental pulp stones, kidney stones, and joint calcifications.

Malacoplakia is a rare chronic inflammatory disease of unknown cause, but a bacterial factor has been strongly implicated. It may be fatal. The disease is characterized by von Kossa staining positive, calcified laminated or target-shaped bodies termed Michaelis-Gutmann bodies which are composed of apatite. The structure of these calcospherules closely resembles calcified nanobacteria.

Tissue calcifications are found in several diseases such as ovarian serous tumor, papillary adenocarcinoma of the endometrium, breast carcinoma, papillary carcinoma of the thyroid, duodenal carcinoid tumor, and craniopharyngioma. In many malignant tumors, needle-shaped crystals are found in epithelial cells. To detect this kind of calcification it is necessary to use electron microscopy, since the crystals are too small to be seen with the light microscope, and their origin is unknown. Many malignant cells have receptors for nanobacterial adherence. They could introduce nanobacteria into the tumor with subsequent calcification. Furthermore, some dividing cells under inflammatory stimuli may have receptors for adherence, e.g., in atherosclerotic plaques known to have calcium phosphate accumulation. In this disease, although electron probe analysis showed that the surface and interior of the mineral deposit had the same chemical composition, SEM revealed different kinds of structures such as spherical particles and fibers which resemble nanobacteria. Similarly, acute periarthritis has been associated with the presence of hydroxyapatite crystals in the joints.

Alzheimer plaques may be labeled with anti-nanobacterial polyclonal antibodies. These polyclonal antibodies contain some autoantibodies, and the present inventors have also obtained some monoclonal autoantibodies in nanobacterial immunizations. Slow bacterial infection has been suggested to play a role in autoimmune diseases. Tissue calcification is often present in these diseases. Nanobacteria are a new example of slowly growing organisms, infecting man for long periods of time. The apatite structure and anomalous nucleic acids may contribute to abnormalities in immune response to this infection.

Several aspects of biogenic apatite nucleation, crystal growth and morphology have been determined both in vivo and in vitro. However, many details remain unresolved, including the specific nature of the initial precipitating phases, the mechanism and factors which control the incorporation of ionic impurities into the crystal lattice, details of the crystallographic ultrastructure and morphology in mineralized tissues (bone, dentine), and the relationship of the inorganic components with the complex collagen based matrix. The reason behind the calcium phosphate deposition in many diseases remain speculative. It has been shown that an accumulation of calcium in mitochondria, which is presumably dependent upon residual substrate for energy production, appeared to cause calcification. Amorphous calcium phosphate in the form of spheroids, and possibly fine fibrils and granules, also appears to play a role in calcification by their transformation into apatite.

SUMMARY OF THE INVENTION

The present invention provides methods for sterilizing articles contaminated with nanobacteria. Such methods according to the present invention will be particularly useful for disinfecting and/or sterilizing medical equipment and solutions used in patient treatment and diagnosis.

The present invention also provides methods of preventing nanobacterial infection, and treating patients infected with nanobacteria. In particular, the present invention provides a method for preventing the recurrence of kidney stones in a patient that has suffered from kidney stones, comprising administration of an antibiotic in an amount effective to inhibit or prevent the growth and development of nanobacteria.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 3. Nanobacteria cultured under SF conditions, and their interaction with cells. (A) Light microscopic micrograph, (B) DNA staining of the same area with the modified Hoechst staining method. (C) Differential interference contrast images of nanobacteria inside a common apatite shelter, and (D) a partly demineralized nanobacterial group (A–D, ×860). (E and F) SEM micrographs of nanobacterial dwellings detached from the culture vessel (Bars=1 $\mu$m). (G) IIFS of internalized mineralized nanobacteria (white arrows) in 3T6 cells. (H) DNA staining of the same area with standard Hoechst method (×540). (I–L) TEM micrographs of intracellular calcifications in 3T6 cells caused by SF-nanobacteria (Bars, I and K=2 $\mu$m, J=500 nm, L=200 nm).

FIG. 8. SEM images of teeth with (A and B), and without (C and D) dental calculi. The tooth shown in (A) was extracted because of periodontal problems, and bone desorption caused by severe dental pulp stone formation. Higher magnification from the area shown by arrow depicts round, and fibrous calcification (B). The tooth shown in (C) was extracted because of an orthodontic problem. This tooth was autoclaved and exposed to DMEM culture medium for one month, in a cell culture condition. No crystallization on the surface was observed (D) Shows the higher magnification of the area marked with an arrow in (C). The vertically cut other half of the same tooth was used for the experiment described in FIG. 9.

FIG. 16: Trimethoprim effect on nanobacteria in 12 days, expressed as minimum inhibitory concentration (MIC).

FIG. 17: Tetracycline effect on nanobacteria in 12 days, expressed as minimum inhibitory concentration (MIC).

FIG. 18: Nitrofurantoin effect on nanobacteria in 12 days, expressed as minimum inhibitory concentration (MIC).

FIG. 19: Doxycyline effect on nanobacteria in 12 days, expressed as minimum inhibitory concentration (MIC).

FIG. 20: Gentamycin effect on nanobacteria in 12 days, expressed as minimum inhibitory concentration (MIC).

FIG. 21: Neomycin effect on nanobacteria in 12 days, expressed as minimum inhibitory concentration (MIC).

FIG. 22: Kanamycin effect on nanobacteria in 12 days, expressed as minimum inhibitory concentration (MIC).

FIG. 23: Vancomycin effect on nanobacteria in 12 days, expressed as minimum inhibitory concentration (MIC).

FIG. 24: Time course of antibiotic effects of 4 $\mu$g/ml of tetracycline, trimethoprim, trimethoprim+sulph, nitrofurantoinh, doxycycline, and positive and negative controls.

FIG. 25: Effect of tetracyline on human nanobacteria. Tetracycline is effective for human nanobacteria isolates similarly compared to the bovine nanobacteria standard strain.

DETAILED DESCRIPTION OF THE PREFERRED EMBODIMENTS OF THE INVENTION

Figure 1H:
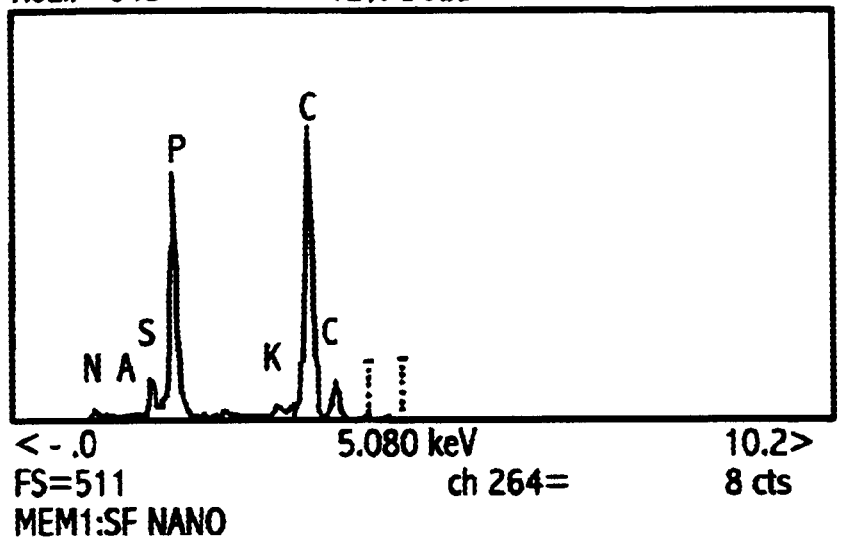
FIG. 1. Light and electron microscopic images of nanobacteria and their analyses with energy-dispersive X-ray microanalysis (EDX). (A) Differential interference constrast image of bottom-attached nanobacteria after a 2-month culture period. (B) DNA staining of the same area (×1600) with the modified Hoechst method. (C) Negative staining of nanobacteria isolated directly from fetal bovine serum (Bar= 200 nm). (D) SEM micrograph showing their variable size (Bar=1 $\mu$m). (E) A dividing nanobacterium covered with a 'hairy' apatite layer (Bar=100 nm). (F) TEM micrograph of nanobacteria buried in an apatite layer after a 3-month-long culture period (Bar=1 $\mu$m), (G) at higher magnification (Bar=200 nm). White central areas in F are artefacts due to loss of the mineral layer in sectioning. (H) Energy-dispersive X-ray microanalysis in SEM of nanobacteria showing Ca and P peaks similar to hydroxyapatite (I).
Figure 1I:
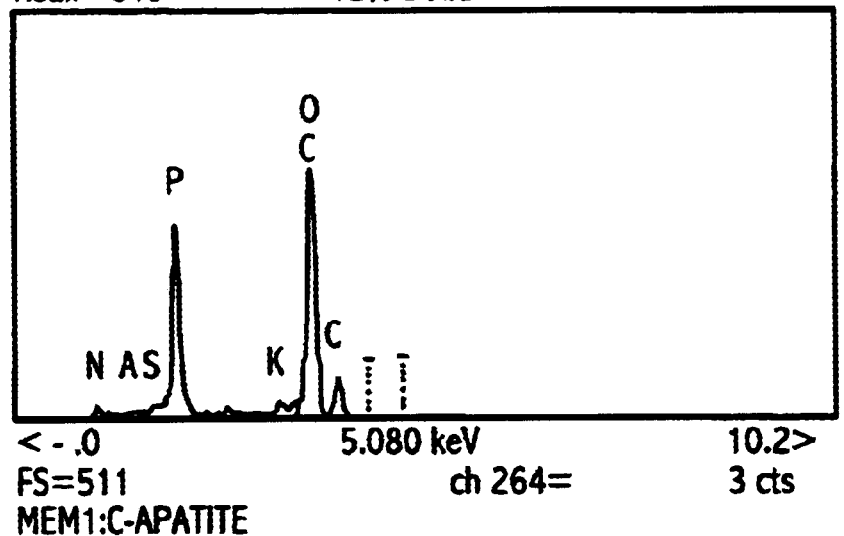

The present inventors have surprisingly discovered the first mineral-coated organism where the mineral constitutes a part of the cell wall essential for survival strategy of the organism. In nanobacteria this mineral is carbonate apatite. As a result, the present inventors have found that any therapeutic agent that is targeted to the apatite may be useful in antinanobacterial therapy.

More particularly, the present invention relates to methods for disinfecting an article contaminated with nanobacteria. As used in the context of the present invention, an article to be disinfected is any article for which complete sterility is desired, including medical devices, surgical tools, and medical and surgical supplies including needles, syringes, tubing, and the like. Also included within the scope of the present invention are solutions for use in medical treatment, and for drug formulation, including sterile water, saline, Ringer's, and other solutions. Any type of mixture, e.g., solution or suspension, can be sterilized by the practice including any formulations for medical treatment or diagnosis, including, but not limited to, any pharmaceutical intended for administration to a patient, including a human or animal.

In a preferred embodiment, the present invention provides a method for disinfecting an article contaminated with nanobacteria comprising exposing the nanobacteria to a disinfectant solution. A disinfectant mixture according to the present invention is preferably a mixture of potassium persulfate and sulfaminoic acid in water, preferably distilled water. The mixture can be a solution, suspension, or the like. In a preferred embodiment, the mixture will be a solution of from about 35% to about 70% potassium persulfate and about 1% to about 15% sulfaminoic acid. In a particularly preferred embodiment, the mixture will be about 50% potassium persulfate and about 5% sulfaminoic acid. This mixture may be used at full strength or may be diluted for use in physiological conditions, preferably to a concentration of about 0.1% to about 10%, most preferably at a concentration of about 1%.

In an alternative embodiment, a disinfectant mixture according to the present invention is a mixture of formaldhyde, glyoxal, glyoxylic acid, and dimethylaurylbenzyl-ammonium chloride in water, preferably distilled water. The mixture can be a solution, suspension, or the like. In a preferred embodiment, the mixture will be a solution of from about 1% to about 10% formaldehyde, about 5 to about 10% glyoxal, about 0.1% to about 5% glyoxylic acid, and about 3% to about 12% dimethylaurylbenzyl-ammonium chloride. In a particularly preferred embodiment, the mixture will be about 4.5% formaldehyde, about 6.8% glyoxal, about 1.5% glyoxylic acid, and about 6% dimethylaurylbenzyl-ammonium chloride. This mixture may be used at full strength or may be diluted for use in physiological conditions, preferably to a concentration of about 0.1% to about 10%, most preferably at a concentration of about 3%.

Alternatively, an article may be decontaminated by demineralization of the nanobacteria followed by exposure to a disinfectant chemical. Demineralization may be accomplished by exposing the nanobacteria to low pH, preferably with a strong acid, preferably hydrochloric acid. Alternatively, demineralization may be accomplished by exposure to a calcium chelator. Suitable calcium chelators for use in the present invention include ethylenediaminetetraacetic acid (EDTA), citric acid, and citrate compounds. In connection with demineralization, any of a broad spectrum of disinfectant chemicals may suitably employed. A particularly preferred disinfectant mixture to be used in connection with demineralization comprise one or more of the following:

| AGENT | Acceptable concentration | Preferred concentration |
|---|---|---|
| ethanol | >50% | >70% |
| glutaraldehyde | >0.1% | >2% |
| formaldehyde | >1% | >4% |
| hypochlorite | >0.1% | >0.5% |
| hydrogen peroxide | >0.1% | >3% |
| hydrochloric acid | >0.1M | >1M |
| sodium hydroxide | >0.1M | >1M |

-continued

| AGENT | Acceptable concentration | Preferred concentration |
|---|---|---|
| sodium dodecyl sulfate (SDS) | >0.1% | >1% |
| Tween 80 | >0.1% | >1% |
| Triton X-100 | >0.1% | >1% |
| guanidium HCl | >1M | >3M |
| urea | >1M | >3M |
| Virkon ® | >0.1% | >1% |
| Erifenol ® | >0.1% | >1.5% |
| Kiorilli ® | >0.1% | >1% |
| Buraton ® | >0.1% | >3% |

Following demineralization, as either an alternative to use of a disinfectant solution, or as an adjunct to the use of disinfectant solution, the article may optionally be autoclaved, preferably at a temperature of at least 121° C., preferably for at least 20 minutes.

Alternatively, following demineralization, as either an alternative to use of a disinfectant solution, or as an adjunct to the use of disinfectant solution, the article may be exposed to ultraviolet radiation, for example, by exposing the article to ultraviolet light approximately equivalent to exposure to a UV-C lamp of at least about 15 W at a distance of about 60 cm or less for at least about 1 hour, preferably for at least about 3 hours, still more preferably, at least overnight. Alternatively, the article may be exposed to at least about three megarads of gamma radiation.

Nanobacteria may also be eradicated from liquids by using sonication. Any conventional sonicator may be used; the sonication times will vary with the power of the sonicator and the volume and characteristics of the liquid to be disinfected. Adequate sonication times may easily be determined by those of ordinary skill in the art without the need for undue experimentation. Typically, sonication of samples from 5–10 minutes will be sufficient to eradicate nanobacteria from most solutions. Sonication can be applied to any sample scale if the ultrasound power and the sample container have suitable ratios to each other. High-power ultrasound sources allow for continuous flow applications as well. The method is applicable in the treatment of any solution. It is gentle for proteins and other subcellular components of the sample if excessive heating is prevented by cooling the solution, either continuously (e.g., by placing the container in which the solution to be disinfected is held into a cold water bath), or by periodically interrupting the sonication process to cool the solution (e.g., by placing the container in which the solution to be disinfected is held into an ice bath).

In a particularly preferred embodiment of the present invention, the nanobacteria are destroyed by drying the article to be disinfected by heating for at least about one hour at a temperature of at least about 100° C. Alternatively, following demineralization as discussed above, the article may be heated for at least about 15 minutes, preferably at least about 30 minutes, to temperatures of at least about 60° C., preferably at least about 100° C.

The present invention further provides tissue culture media formulated to be free of nanobacteria. Said nanobacteria-free tissue culture media may be any standard tissue culture media available to the skilled artisan, additionally comprising a nanobacteria-antibiotic-effective amount of one or more antibiotics selected from the group consisting of β-lactam antibiotics, aminoglycoside antibiotics, tetracycline antibiotics, and mixtures thereof. Suitable β-lactam antibiotics for use in the present invention include, but are not limited to, penicillin, phenethicillin, ampicillin, azlocillin, bacmpicillin, carbenicillin, cylclacillin, mezlocillin, piperacillin, epicillin, hetacillin, cloxacillin, dicloxacillin, methicillin, nafcillin, oxacillin, and salts thereof. Suitable aminoglycoside antibiotics for use in the present invention include, but are not limited to, streptomycin, kanamycin, gentamycin, amikacin, neomycin, pardomycin, tobramycin, viomycin, and salts thereof. Suitable tetracyclines include tetracycline, chlortetracycline, demeclocycline, doxycycline, methacycline, oxytatracycline, rolitetracycline, minocycline, sancycline, and pharmaceutically acceptable salts thereof. Additionally, prior to use, a culture medium according to the present invention is preferably sterilized according to one of the methods set forth above. The ordinary skilled artisan may select the method of sterilization most suitable to the particular culture medium.

The present invention also provides a method for preventing the development of calcifications in vivo, i.e., in a patient in need of such treatment, comprising administering an antibiotic to the patient in an amount effective to inhibit or prevent the growth of nanobacteria. In the context of the present invention, in vivo calcifications includes, but is not limited to, kidney stones, atherosclerosis, acute periarthritis, dental pulp stones or denticles, malacoplakia, Alzheimer's disease, autoimmune disease including scleroderma, and metastatic and tumoral calcification found in hemodialysis patients and calciphylaxis, malignant tumors including ovarian serous tumor, papillary adenocarcinoma of the endometrium, breast carcinoma, papillary carcinoma of the thyroid, duodenal carcinoid tumor, and craniopharyngioma. In the context of the present invention, a "patient" is any mammal, preferably a human, suffering from tissue calcification, especially in connection with one of the disorders listed above.

In a preferred embodiment, the present invention provides a method for preventing the development of calcifications in vivo in a patient in need of such treatment comprising administering an antibiotic nanobacteria-antibiotic-effective amount of one or more antibiotics selected from the group consisting of β-lactam antibiotics, aminoglycoside antibiotics, tetracyclines, and pharmaceutically acceptable salts thereof, and mixtures thereof. Suitable β-lactam antibiotics for use in the present invention include, but are not limited to, penicillin, phenethicillin, ampicillin, azlocillin, bacmpicillin, carbenicillin, cylclacillin, meziocillin, piperacillin, epicillin, hetacillin, cloxacillin, dicloxacillin, methicillin, nafcillin, oxacillin, and pharmaceutically acceptable salts thereof. Suitable aminoglycoside antibiotics for use in the present invention include, but are not limited to, streptomycin, kanamycin, gentamycin, amikacin, neomycin, pardomycin, tobramycin, viomycin, and pharmaceutically acceptable salts thereof. Suitable tetracyclines include tetracycline, chlortetracycline, demeclocycline, doxycycline, methacycline, oxytatracycline, rolitetracycline, minocycline, sancycline, and pharmaceutically acceptable salts thereof. In a particularly preferred embodiment, antibiotics are coadministered with citrate compounds.

In an alternative embodiment, Vitamin K, and/or its analogs, may be employed in the methods of the present invention. Suitable Vitamin K analogs for use in the present invention include, but are not limited to, menadione, phytonadione (vitamin $K_1$), and pharmaceutically acceptable salts thereof. For use in the present invention, Vitamin K is preferably employed in a concentration of at least 1 μg/ml.

In a further embodiment, p-amino salicylic acid, as well as other salicylic acid derivatives may be used in the method of the present invnetion. Particularly preferred is acetylsalicylic acid (i.e., Aspirin).

In a further embodiment, bisphosphonates may be employed in the methods of the present invention. As a family, bisphosphonates are characterized pharmacologically by their ability to inhibit bone resorption, whereas, pharmacokinetically, they are classified by their similarity in absorption, distribution, and elimination.

Although all bisphosphonates have similar physicochemical properties, their antiresorbing activities differ. Activity is dramatically increased when the amino group is contained in the aliphatic carbon chain. For example, alendronate, an aminobisphosphonate, is approximately 700-fold more potent than etidronate, both in vitro and in vivo. In general, bisphosphonates are poorly absorbed from the gastrointestinal tract as a result of their poor lipophilicity. In vitro and in vivo studies have shown that bisphosphonates are absorbed from the gastrointestinal tract via paracellular transport. Systemically available bisphosphonates disappear very rapidly from plasma, and are partly taken up by the bone and partly excreted by the kidney. The relative contribution of these two processes to overall plasma elimination differs among bisphosphonates. To date, all bisphosphonates studied show no evidence of metabolism. Renal excretion is the only route of elimination. Studies with alendronate in rats indicate that the drug is actively secreted by an uncharacterized renal transport system, and not by the anionic or cationic renal transport systems.

Bisphosphonates have a P—C—P bond instead of the P—O—P bond of inorganic pyrophosphate that makes them resistant to enzymatic degradation and gives them a high affinity for hydroxyapatite. They are potent blockers of osteoclastic bone resorption and have been successfully used to treat metabolic bone diseases that involve increased bone resorption. It is possible to synthesize a variety of bisphosphonates by substituting the hydrogen on the carbon atom. Suitable bisphosphonates for use in the present invention include, but are not limited to, alendronic acid, etidronic acid, clodronic acid, oxidronic acid, and pharmaceutically acceptable salts thereof. For use in the present invention, bisphosphonates are administered preferably at a dose of approximately 5–20 mg/kg/day.

A still further part of this invention is a pharmaceutical composition of matter suitable for prevention of calcifications in vivo that comprises at least one or more of the compounds set forth above, mixtures thereof, and/or pharmaceutical salts thereof, and a pharmaceutically-acceptable carrier therefor. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

For therapeutic use in the method of the present invention, an antibiotic, or its salt, can be conveniently administered in the form of a pharmaceutical composition containing one or more antibiotics, or salts thereof, and a pharmaceutically acceptable carrier therefor. Suitable carriers are well known in the art and vary with the desired form and mode of administration of the pharmaceutical composition. For example, they may include diluents or excipients such as fillers, binders, wetting agents, disintegrators, surface-active agents, lubricants, and the like. Typically, the carrier may be a solid, liquid, or vaporizable carrier, or combinations thereof. Each carrier must be "acceptable" in the sense of being compatible with the other ingredients in the composition and not injurious to the patient. The carrier must be biologically acceptable and inert, i.e., it must permit the antibiotic compound(s) to inhibit the development of nanobacteria and, particularly, the apatite crystals associated with nanobacteria.

Antibiotic compounds for use in the method of the present invention, or salts thereof, may be formulated together with the carrier into any desired unit dosage form. Typical unit dosage forms include tablets, pills, powders, solutions, suspensions, emulsions, granules, capsules, and suppositories; tablets and capsules are particularly preferred. Formulations include those suitable for oral, rectal, nasal, topical (including buccal and sublingual), vaginal and parenteral (including subcutaneous, intramuscular, intravenous, intradermal, and transdermal) administration, with formulations appropriate for oral administration being preferred.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol, sorbitate esters, and the like. In these instances, adequate amounts of isotonicity adjusters such as sodium chloride, glucose or glycerin can be added to make the preparations isotonic. The aqueous sterile injection solutions may further contain anti-oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

A compound for use in the present invention may be present in the composition in an broad proportion to the carrier. For instance, the compound may be present in the amount of 0.01 to 99.9 wt %, and more preferably in about 0.1 to 99 wt %. Still more preferably, the compound may be present in an amount of about 1 to 70 wt % of the composition.

The dosage of the antibiotics, pharmaceutically acceptable salts thereof, or mixtures thereof, administered to a patient according to the present invention will vary depending on several factors, including, but not limited to, the age, weight, and species of the patient, the general health of the patient, the severity of the symptoms, whether the composition is being administered alone or in combination with other therapeutic agents, the incidence of side effects and the like.

In general, a dose suitable for application in the method of the present invention is about 0.001 to 100 mg/kg body weight/dose, preferably about 0.01 to 60 mg/kg body weight/dose, and still more preferably about 0.1 to 40 mg/kg body weight/dose per day. The desired dose may be administered as 1 to 6 or more subdoses administered at appropriate intervals throughout the day. The antibiotic compounds may be administered repeatedly over a period of months or years, or it may be slowly and constantly infused to the patient. Higher and lower doses may also be administered.

The daily dose may be adjusted taking into account, for example, the above-identified variety of parameters. Typically, the present compositions may be administered in an amount of about 0.001 to 100 mg/kg body weight/day. However, other amounts may also be administered. To achieve good plasma concentrations, the antibiotics may be administered, for instance, by intravenous injection of an approximate 0.1 to 1% solution of the antibiotics, optionally in saline, or orally administered as a bolus.

The active ingredient may be administered for therapy by any suitable routes, including topical, oral, rectal, nasal, vaginal and parenteral (including intraperitoneal, subcutaneous, intramuscular, intravenous, intradermal, and transdermal) routes. It will be appreciated that the preferred route will vary with the condition and age of the patient, the nature of the disorder and the chosen active ingredient including other therapeutic agents. Preferred is the oral route. Also preferred is the intravenous route. However, other routes may also be utilized depending on the conditions of the patient and how long-lasting the treatment is.

While it is possible for the antibiotic(s) to be administered alone, it is preferably present as a pharmaceutical formulation. The formulations of the present invention comprise at least one antibiotic, as defined above, together with one or more acceptable carriers thereof and optionally other therapeutic agents.

The above method may be practiced by administration of the compounds by themselves or in a combination with other antibiotics, including other therapeutic agents in a pharmaceutical composition. Other therapeutic agents suitable for use herein are any compatible drugs that are effective by the same or other mechanisms for the intended purpose, or drugs that are complementary to those of the antibiotics listed above. The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified.

EXAMPLE 1

Mineralization by Nanobacteria

In this study, the present inventors provide evidence that nanobacteria can act as crystallization centers (nidi) for the formation of biogenic apatite structures. The mineralization process was studied in vitro with one bovine isolate from commercial fetal bovine serum and with a human isolate. These findings are of concern in medicine because nanobacterial bacteraemia occurs in humans, and nanobacterial nidi might initiate pathological calcification.

Materials and Methods
Culture Methods for Nanobacteria.

Nanobacteria were cultured in DMEM (GIBCO) under mammalian cell culture conditions (37° C.; 5–10% $CO_2$/90–95% air). Serum was used at 10% final concentration as the supplement and source of nanobacteria, which were fetal bovine serum (Sera Lab, lot 901045), or human serum from a 29-years-old Finnish male. The cultures were prepared using strict aseptic techniques in a cell culture facility. Nanobacterial samples were filtered through 0.2 μm filters before culturing. Subcultures were made using either the same serum or γ-irradiated fetal bovine serum (γ-FBS) as a culture supplement. Fetal bovine serum and nanobacteria were γ-irradiated, when indicated, at a minimum dose of 30 kGy given at room temperature during about 16 hr by Kolmi-Set (Ilomantsi, Finland).

Subculturing of nanobacteria in serum-free (SF) DMEM was performed with monthly passages 1:11 for five years. SF-nanobacteria attach firmly to the bottom of the culture vessel. These cultures were passaged or harvested with a rubber scraper. Cultures were established on Loeffler medium supplemented with 10% conditioned medium from nanobacterial culture, and DMEM replaced water in the formula. The incubation period was 6 weeks under cell culture conditions.

Only pure nanobacterial cultures were used. Positive identification of nanobacteria involved typical growth rates and optical properties, specific stainability with Hoechst 33258 and with indirect immunofluorescence staining (IIFS), as described below. Control experiments were performed to determine whether spontaneous crystallization could occur in a culture medium. The medium was incubated with or without γ-FBS or γ-irradiated nanobacteria. Neither mineralization nor nanobacteria multiplication was observed even during the 6-month follow-up.

Preparation and Infection of 3T6 Cells.

3T6 cells (ATCC CCL 96) were cultured on coverslips. SF-nanobacterial cultures were scraped and 100 μl portions were added to the cell cultures and incubated for 24 hr in the incubator. Only DMEM was added to the control experiments. Transmission electron microscopy (TEM), IIFS, and DNA and von Kossa staining were used for the observation of the cell-SF nanobacteria interaction.

Kidney Stones.

Thirty randomly collected kidney stones (K-SKS, Stone Analysis Central Laboratory, Finland) were demineralized in 1N HCl and then neutralized, centrifuged at 14,000×g for 15 min, and the pellets were used for IIFS and TEM. Part of the pellets were suspended in DMEM, sterile-filtered and cultured in DMEM supplemented with γ-FBS under nanobacterial culture conditions.

Staining Methods.

DNA staining with Hoechst 33258 fluorochrome was carried out as described in Hoechst Stain Kit, Flow Laboratories, except, where indicated, increasing the stain concentration from 0.5 μg/ml to 5 μg/ml. IgG1 class anti-nanobacterial monoclonal antibodies (mAb), Nb 8/0 and Nb 5/2, were used in IIFS. The epitope of the latter mAb was inactivated by incubating it in sodium borohydrate (3×1 min; 0.5 mg/ml in PBS), when indicated, to test specificity of the binding. The samples were viewed under a Nikon Microphot-FXA microscope with fluorescence and differential interference contrast (DIC) optics. Specific calcification detection was performed with von Kossa staining. 3T6 cells exposed to SF-nanobacteria for 48 hr were used as samples.

Electron Microscopy and Energy Dispersive X-ray Microanalysis.

For negative staining, nanobacteria were isolated by centrifugation at 40000 g for 1 hr directly from fetal bovine serum diluted 1:5 in PBS. A carbon-coated 400 mesh copper grid was placed on a drop of the suspension of nanobacteria in PBS for 1 min, washed with water, and stained on a drop of 1% phosphotungstic acid for 90 sec. Scanning electron microscopy (SEM) and TEM were performed. The topographic features of the nanobacteria were investigated with a SEM equipped with energy-dispersive X-ray microanalysis (EDX). Hydroxyapatite (Sigma, No-H-0252, St. Louis, Mo.) was used as a reference.

Fourier Transform IR Spectroscopy (FTIR), Chemical Analysis, and Enzyme Assays.

Hydroxyl and carbonate groups in the apatite minerals were detected using FTIR by K-SKS, Stone Analysis Central Laboratory, Finland, following standard methods. Chemical analysis of nanobacteria was carried out by analyzing urease enzyme activity and alkaline phosphatase(AP) with p-nitrophenylphosphate as substrate at pH 9.5.

Results

Culture Properties, Morphology, and Apatite Formation by Nanobacteria in Serum-containing Media.

Light microscopy with DIC revealed barely detectable nanobacteria near the bottom of the culture vessel after about a one week culture period. In two weeks, nanobacteria appeared as groups easily visible in microscopy. After one month, many were in clumps and started to attach to the bottom of the culture vessel, and by the end of two months, most were in a white-colored biofilm visible to the naked eye. The criteria for pure nanobacterial culture were refractile aggregates of typical coccoid-shaped particles (FIG. 1A), showing DNA stainability (FIG. 1B) only with the modified method, a negative culture result on sheep-blood agar and IIFS positivity with anti-nanobacteria mAbs.

Negative-staining of nanobacteria in uncultured fetal bovine serum revealed 0.2–0.3 μm coccoid particles (FIG. 1C). After a one-month culture period, SEM revealed similar coccoid shape with a diameter of 0.2 to 0.5 μm (FIG. 1D). Their rough surfaces resembled those seen in TEM (FIGS. 1E–G). During longer culture periods, they were mostly attached to the culture vessel and finally were in a mineral layer (FIGS. 1F and G). Chemical analysis using EDX gave similar Ca and P peaks as detected for hydroxyapatite (FIGS. 1H and I). Cultures of the human isolate gave identical results (not shown). Chemical analysis of nanobacteria harvested after a 3-month culture period revealed a high content of inorganic material. The pellet dry weight varied from 23% to 39% and consisted of: N (1–1.3%); P (12.3–14.6%); Ca (23.4–23.5%); Mg (1.4–1.9%); K (0.1%); and Na (1.2–1.4%). FTIR revealed that carbonate apatite was present in samples from all culture ages between 7–180 days in both human and bovine nanobacteria. Control hydroxyapatite was correctly identified in the test. The analytical methods do not exclude the possible presence of minor quantities of other mineral phases. To exlude that possibility, crystallographic analysis are needed. Nanobacteria did not produce urease or AP activity, and their culture medium remained at pH 7.4.

Apatite Formation by Nanobacteria in Loeffler Medium.

Figure 2A:
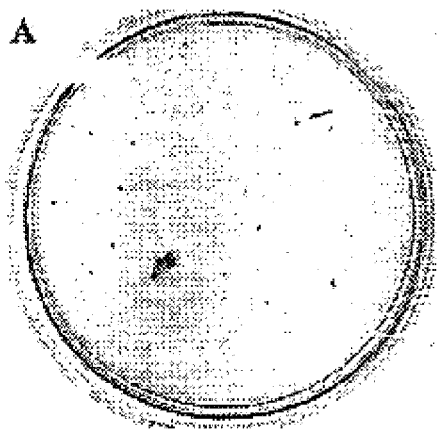
FIG. 2. Nanobacterial stony colonies, and comparison with hydroxyapatite.(A) Colonies on modified Loeffler medium in a 10 cm plate. The colonies penetrated through the medium forming stony pillars. Arrow shows one typical greyish-brown colony depicted in B (×40). (C) Needle-like crystal deposits in the pillar revealed by TEM (Bar=200 nm). (D) TEM image of reference apatite crystals (Bar=100 nm).
Figure 2B:
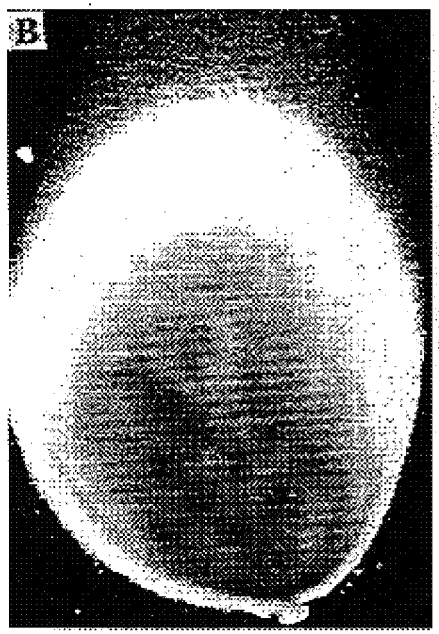
Figure 2C:
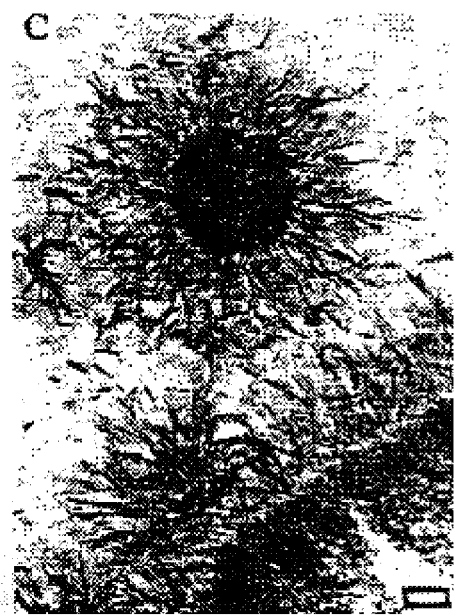
Figure 2D:

Macroscopic nanobacterial colonies on modified Loeffler medium (FIGS. 2A and B) were stony, greyish-brown, passagable and penetrated the medium layer and attached to the bottom of the culture vessel after 6 weeks of culture. IIFS with anti-nanobacteria mAbs (data not shown), and TEM revealed nanobacteria coated in needle-like apatite crystals (FIG. 2C), similar to the hydroxyapatite crystals (FIG. 2D).

Apatite Formation by Nanobacteria in SF-medium.

When washed nanobacterial pellets or SF-nanobacteria were subcultured in SF-DMEM, bottom-attached coccoid organisms were observed within one day. Differential interference contrast microscopy revealed a several-micrometer-thick mineral layer around each nanobacteria reaching a yeast-size within one week (FIG. 3A). Their morphology differed extensively from the coccoid nanobacteria, but similar DNA stainability was observed (FIG. 3B). They produced biomass at about half the rate observed in serum containing cultures. The metabolic incorporation of [$^{35}$S] methionine and [5-$^3$H]uridine is proof that they were replicating. Differential interference contrast microscopy revealed nanobacterial multiplication inside the mineral formations (FIG. 3C). These apatite shelters, were shown in SEM to have a hollow interiors, were apparently the dwelling-place of the organisms (FIGS. 3E and F). The size of the cavity is probably dependent on the number of nanobacteria it contains (FIG. 3F). Apparently, the openings of the cavities were facing the bottom of the culture vessel before scraping. Thus, the apatite shelters provided complete protection for the organisms. The cultures could be passaged monthly for over 5 years and always followed a similar growth pattern. After addition of γ-FBS, these nanobacterial formations returned to the forms found in serum cultures (see FIG. 3D). That the shelters were apatite in nature was proven by EDX. FTIR determined that it was carbonate apatite. The human isolate produced similar formations.

Intra- and Extracellular Calcification in Fibroblast Cultures.

Figure 4A:
FIG. 4. Examples of extra- and intracellular calcification by nanobacteria. (A) TEM micrograph of cultured nanobacteria (Bar=20 nm) from fetal bovine serum, and (B) a bacterium in a kidney stone after demineralization (Bar=50 nm). (C) IIFS of the same kidney stone with anti-nanobacteria mAb. (D and E) von Kossa staining results of 3T6 cells exposed to SF-nanobacteria for 24 hr, and (F) negative control (×270).
Figure 4B:
Figure 4C:
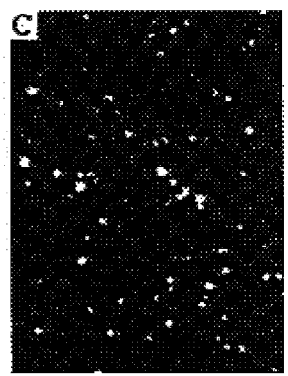
Figure 4D:
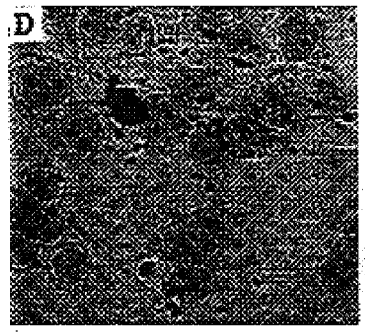
Figure 4E:
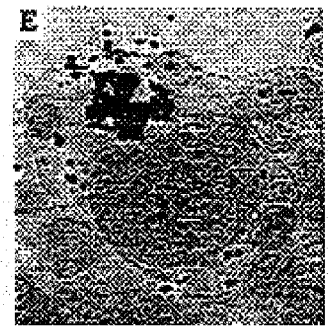
Figure 4F:

3T6 cells infected for 48 hr with SF-nanobacteria showed altered cell morphology, e.g., large vacuolization with internalized SF-nanobacteria (FIG. 3G). Control cells were negative (not shown). Standard DNA staining of the nanobacteria-infected cells revealed no ordinary contamination (FIG. 3H). TEM occasionally revealed SF-nanobacteria adhering to the cell surface, but mostly they were in various compartments within the cells (FIGS. 3I–L), including nucleus (not shown). von Kossa staining revealed intra- and extracellular calcification in these cells (FIGS. 4D and E). Heavily infected cells showed nuclear abnormalities, e.g., macronucleus, as shown in FIG. 4E, and abnormal nuclear shape (FIGS. 3G, H, K and L). Control cells were von Kossa negative and did not have nuclear abnormalities (FIG. 4F).

Detection of Nanobacterial Antigens in Kidney Stones.

The present inventors supervised a survey on 30 human kidney stones in an attempt to detect the presence of nanobacteria. Nanobacteria-specific mAb revealed positive, nanobacteria-sized cocci at various concentrations in all 30 demineralized stones using IIFS. An image of a relevant sample is seen in FIG. 4C. The results were repeated with another nanobacteria-specific mAb, Nb 5/2, that detects a carbohydrate epitope, and antibody binding could be abolished with sodium borohydrate treatment, which destroys carbohydrate antigens. Specificity was further proven with negative staining results with 4 different mAbs (IgG1 class) detecting nonrelevant antigens (data not shown). Bacteria of similar size and morphology (FIG. 4B) as nanobacteria (FIG. 4A) were found with TEM in strongly positive stones (FIGS. 4B and C). In nanobacterial culture conditions, sterile-filtered extracts of all the stones revealed microorganisms having the growth rate, morphology, mineralization, and staining properties of nanobacteria.

Discussion

The present inventors have found nanobacterial culture systems that allow for reproducible production of apatite calcification in vitro. Depending on culture conditions, tiny nanocolloid-sized particles covered with apatite, or biofilm, sand, stones and tumor-like growths of apatite could be produced (Table 1).

TABLE 1

Culturability of nanobacteria and apatite formation

| Culture condition | Replication | Size | Apatite and its form |
|---|---|---|---|
| Serum | + | S | +, nanocolloid |
| 10–50% serum in DMEM | + | S | ++, nanocolloid |
| DMEM | + | L | +++, sand |
| 50% DMEM – 50% urine | + | L | +++, sand |
| Urine | +/− | n.e. | n.e. |
| Modified Loeffler medium | + | L | +++, tumor-like |

S, small size (200–400 nm);
L, large size (1 μm to 1 mm, including the mineral);
n.e., not evaluated because of crystal formation.
Pluses in the last column refer to amount.

The principal precondition for mineralization was low levels of intact serum in the culture medium. Serum contains powerful proteinaceous inhibitors of apatite crystal formation, osteopontin, osteocalcin and fetuin, which may account for the observed inhibition and even dissolution of the formed minerals after replenishment of fetal bovine serum. In cases of nanobacterial cultures in serum containing medium, the inhibitors permitted only marginal mineralization. Mineralization increased in parallel with the dilution of the serum in cell culture medium. Finally, in SF-medium, apatite formation was extensive and rapid. Although modified Loeffler medium contains 75% serum, the serum proteins were denatured during the sterilization steps. Thus, apatite formation was not inhibited resulting in solid apatite colonies about 1–5 mm in diameter in 6 weeks. Living nanobacteria are needed to produce apatite in the nanobacterial model. γ-Irradiated nanobacteria did not multiply and, although they could gather apatite on them, no sizable calcification was produced even after 6-month long incubations.

Chemical analysis revealed that the overall composition of biofilm and solid mineral formation was similar to that of bone, except carbonate apatite was formed, as in most extraskeletal tissue calcification and stones whereas in bone, hydroxyapatite is the prevalent form. In the nanobacterial model, apatite was formed at [Ca] 1.8 mM and [$P_i$] 0.9 mM or less, without replenishment of the medium.

Nanobacteria were found in all 30 human kidney stones that thes inventors have screened. Previously, only struvite stones (4–15% of all kidney stones) composed of magnesium ammonium phosphate and small amounts of apatite have been regarded as deriving from bacteria. They are formed in vitro and probably in vivo by Proteus, Staphylococci and E. coli that produce urease, elevating the local pH to more lithogenic levels. Alkaline phosphatase may augment the lithogenicity. Nanobacteria do not produce urease or AP, but nucleate carbonate apatite directly on their surfaces at pH 7.4 suggesting the presence of nucleating molecules. Since nanobacteria are culturable under physiological conditions in media similar in composition to glomerular filtrate, nanobacteria offer a unique model for kidney stone formation.

EXAMPLE 2

Eradication of Nanobacteria

The selection of an appropriate test for nanobacterial disinfection is not straightforward, and accurate comparisons of the results obtained from different tests are problematic, due to the number of factors affecting disinfection. These factors include duration of exposure, presence of organic load, type, age, concentration and diluent of the disinfectant, and number, age, growth form of the microorganisms present, and the temperature. Currently there are several types of disinfection tests, but these are mainly suitable for rapidly growing bacteria. The disinfection tests of slowly growing Mycobacteria, some of which are extremely resistant, have long suffered from lack of appropriate, reliable standardization. Typically, centrifugation or very high dilution have been used to eliminate the effect of residual concentrations of disinfectants. Subsequently, plating on agar medium for colony count is done for evaluating the reduction in viability. For nanobacteria such assays are not suitable. Recovery of nanobacteria by centrifugation generally results in unpredictable losses. Due to their slow growth rate, high dilutions result in very long incubation times, and extremely poor culturability on solid media makes the evaluation of a nanobacteria count impossible.

Mineralization is the most characteristic property of nanobacteria, and possibly the main mechanism of pathology caused by the organism. The mineral formed under standard culture conditions is hydroxyl or carbonate apatite as revealed by several methods, including energy dispersive X-ray microanalysis and Fourier transform IR spectroscopy. One of the primary functions of the mineral may be protection against harsh environmental conditions. The apatite can prevent the penetration of harmful compounds to the interior of the organism. Depending on the culture time and culture conditions, various degrees of mineralization has been observed. Mineralization by nanobacteria cultured without serum (SF-nanobacteria) is much more extensive than that observed in nanobacteria cultured with serum containing medium. The doubling time of serum nanobacteria and SF-nanobacteria, are about three days and six days respectively, measured by amino acid incorporation.

Disinfecting chemicals at concentrations generally used have now been tested against cultured nanobacteria. The chemicals selected represent a wide variety of mechanisms which are known to affect biological systems. Survival of nanobacteria at high temperature, in drying and under UV-C irradiation was also tested. There are several mechanisms for antibiotic resistance in bacteria which have not been discussed here. The present inventors evaluated the effect of four antibiotics against nanobacteria. The antibiotics are those commonly used in cell culture.

Experimental Design
Nanobacteria Culture in Serum Containing Medium

Nanobacteria were cultured with 10% fetal bovine serum in DMEM medium (serum nanobacteria) for one month at 37° C. in an atmosphere of 5% $CO_2$–95% air. The cultures were harvested by centrifugation. For the autoclaving, UV, microwave, heating and drying treatments, the harvested nanobacteria were suspended in phosphate buffered saline (pH 7.4; PBS). After treatments, subculturing of the nanobacteria was made in 10% gamma irradiated fetal bovine serum in DMEM medium. The growth of serum nanobacteria was followed by light microscopy and absorbance measurement with a spectrophotometer at 650 nm.
Nanobacteria Culture Without Serum SF-nanobacteria were cultured in DMEM medium for one week at 37° C. in an atmosphere of 5% $CO_2$–95% air, and all the cultures firmly adhered to the culture vessel. The cultures were exposed to the disinfectants after removal of the culture medium. For the autoclaving, UV, microwave, and drying treatments, the medium was removed and an equal amount of PBS used instead. For the heat treatments, the SF-nanobacteria were harvested by scraping the culture vessel followed by centrifugation of the medium. The obtained pellet was suspended in PBS and used in the test. After treatments the SF-nanobacteria were subcultured in DMEM medium and the growth followed by light microscopy to see the adherence and typical mineralization.
Chemical Disinfection for SF-nanobacteria The concentrations of the chemicals used were those commonly used for disinfection or as instructed by the manufacturer. The chemicals included 70% ethanol, 2% glutaraldehyde, 4% formaldehyde, 0.5% hypochlorite, 3% hydrogen peroxide, 1 M hydrochloric acid (HCl), 1M sodium hydroxide (NaOH), 1% sodium dodecyl sulfate (SDS), 1% Tween 80, 1% Triton X-1 00, 3M guanidium-hydrochloride, 3M urea, 1% Virkon® (Antec International Ltd., Suffolk, England; 100% product contains 50% potassium persulfate, 15% sodium alkyl benzene sulphonate, and 5% sulfaminoic acid), 1.5% Erifenol® (Orion OY, Finland; 100% product contains <5% NaOH, <5% o-benzyl-p-chlorophenol, 5–15% p-chloro-m-cresol), 1% Klorilli® (Orion OY, Finland; 100% product contains sodium metasilicate, sodium N-chloro-p-toluenesulfonamide-3-hydrate and 20,000 ppm active chlorine), and 3% Buraton® (Schülke & Mayr, Germany; 100% product contains 4.5% formaldehyde, 6.8% glyoxal, 1.5% glyoxylic acid, 6% dimethylaurylbenzyl-ammonium chloride). The dilutions to be used were freshly prepared on the day of exposure in sterile distilled water. As a positive control, only diluent was used. Negative control contained only culture medium.

The SF-nanobacteria were exposed to the chemicals for 10 and 30 minutes at room temperature after removal of the culture medium. After exposure, the disinfectant solution was removed and fresh medium added (with a neutralization step in the case of HCl and NaOH). If any significant deattachment occurred, nanobacteria were recovered by centrifugation, and subcultured. The exposed serum-free cultures were passaged 1:10 after 48 hours and the growth was followed by light microscopy for three weeks.
Autoclaving, UV, and Drying Treatments Serum and SF-nanobacteria were autoclaved in a small volume of phosphate buffered saline (PBS), pH 7.4 at 121° C. for 20 minutes. UV treatment was given to both nanobacteria in PBS in a laminar hood under Philips 15 W UV-C lamp for periods of 1 and 3 hours and overnightly in petri dishes with the lids removed. The distance of the cultures from the lamp was about 60 cm. Drying treatments were carried out by drying nanobacteria overnightly at room temperature or by heating for one hour at 100° C. SF-nanobacteria was dried only overnightly at room temperature. Microwave treatment was given by bringing the samples ten times to boiling point (100° C.) in a 1400 W microwave oven.
Heating of Nanobacteria Heat effect on survival of the nanobacteria was determined by exposing nanobacteria as pellets in PBS for 15 and 30 minutes, with temperatures varying between 60° C. and 100° C. Exposed SF-nanobacteria were cultured in DMEM medium and the growth followed by microscopy as above. The growth of serum nanobacteria cultures was followed by light microscopy and absorbance measurement with a spectrophotometer at 650 nm.
Antibiotic Sensitivity Tests Antibiotic sensitivity of serum nanobacteria was tested with a mixture of penicillin (β-lactam) and streptomycin (aminoglycoside) (PS) at 1× and 10×concentration (100 IU penicillin, 100 µg/ml streptomycin=1×), kanamycin (aminoglycoside) at 1× and 10×concentration (100 µg/ml= 1×) and gentamycin (aminoglycoside) at 1× concentration (100 μg/ml). The 1×concentrations are those recommended for cell culture. After 10 days culture in 10% serum containing DMEM with the antibiotic, growth was compared to that of nanobacteria cultures without antibiotics present.

Results

Chemical Disinfection

SF-nanobacteria showed a wide resistance to the disinfectants used. Only Virkon was effective in killing SF-nanobacteria after thirty minutes. Hydrochloric acid treatment dissolved the apatite layer of nanobacteria, but remineralization was observed after addition of culture medium. The guanidium-hydrochloride and Buraton treatments resulted in the deattachment of the SF-nanobacteria, but the disinfection efficacy of Buraton was slightly less than that of guanidium-hydrochloride. Results of the chemical treatments are presented in Table 2. Survival was determined after subculture by comparison to the treatment with only diluent.

Autoclaving, UV, and Drying Treatments

Drying at a temperature of 100° C. killed serum nanobacteria, but drying at room temperature did not. Autoclaving was not detrimental to the SF-nanobacteria, but a marked reduction in the survival of serum nanobacteria was observed. SF-nanobacteria tolerated UV light with no

TABLE 2

Resistance of SF-nanobacteria to chemical disinfectants.

| | Exposure Time | |
|---|---|---|
| Chemical | 10 min | 30 min |
| 70% ethanol | +++ | +++ |
| 2% glutaraldehyde | +++ | +++ |
| 4% formaldehyde | +++ | +++ |
| 0.5% hypochlorite | +++ | +++ |
| 3% $H_2O_2$ | +++ | +++ |
| 1M HCl | n.d. | ++* |
| 1M NaOH | +++ | +++ |
| 1% SDS | +++ | +++ |
| 1% Tween 80 | +++ | +++ |
| 1% Triton X-100 | +++ | +++ |
| 3M Guanidium HCl | n.d. | θ = |
| 3M Urea | +++ | +++ |
| 1% Virkon ® | n.d. | −* |
| 1.5% Erifenol ® | +++ | +++ |
| 1% Klorilli ® | +++ | +++ |
| 3% Buraton ® | n.d. | ++* |

+++: No effect;
++: Reduced survival;
+: Markedly reduced survival;
−" No survival;
*= partial or total detachment on exposure;
n.d. = not determined effect on growth, but serum nanobacteria was significantly inactivated. Nanobacteria samples dried during the overnight UV treatment, and thus there became an additional stress for the organisms. Drying obviously had little or no effect to the result, since the survival of nanobacteria with all the UV treatments was similar. Because of lack of an UV radiometer, no UV dosage could be calculated, and more accurate tests with nanobacteria in culture medium should be conducted. Microwave treatment was more like a heat shock treatment than a sterilization step, short boilings being completely ineffective. Results of the follow-up of the nanobacteria survival after autoclaving, UV, microwave and drying treatments are presented in Table 3. SF-nanobacteria was much more resistant than nanobacteria cultured with serum. SF-nanobacteria survived all test conditions without a marked reduction in viability. Serum nanobacteria were killed by drying for one hour at 100° C., and survival was markedly reduced in all other test conditions.

TABLE 3

Survival of nanobacteria after physical exposure.

| Treatment | Survival of serum nanobacteria | Survival of serum-free nanobacteria |
|---|---|---|
| Autoclave | + | +++ |
| UV irradiation (1 h) | + | +++ |
| UV irradiation (3 h) | + | +++ |
| UV irradiation (overnight) | + | +++ |
| Microwaves | +++ | +++ |
| Drying (RT) | + | +++ |
| Drying (100° C.) | − | n.d. |

Figure 5:
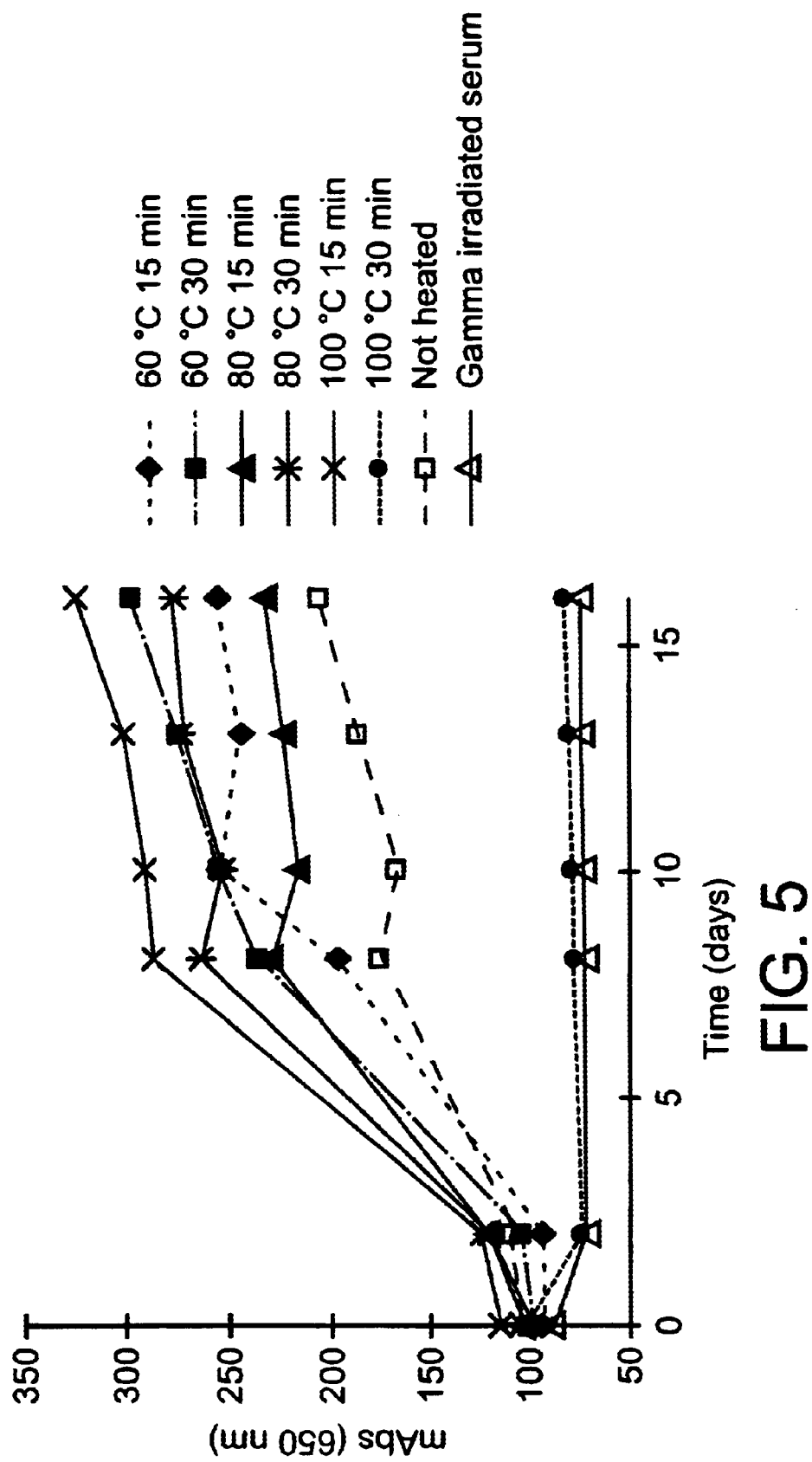
FIG. 5. Graphic showing the effect of heat on the growth of serum nanobacteria. Nanobacteria were exposed for heat in PBS and cultured for 16 days. Only thirty minutes boiling resulted in the inactivation of nanobacteria. Exponential growth was observed with all other treatments. The medium containing 10% gamma irradiated serum (Negative control) did not show any grow.

+++: No effect;
++: Reduced survival;
+: Markedly reduced survival;
−: No survival;
* = partial or total detachment on exposure;
n.d. = not determined Heat Resistance of Nanobacteria Nanobacteria were very heat resistant. Fifteen minutes boiling was not enough for killing serum nanobacteria, but thirty minutes inactivated them. Growth curves of serum nanobacteria after heat treatment are presented in FIG. 5. Importantly, the growth of serum nanobacteria was very similar, with no observed lag period, even after the fifteen minute boiling. Microscopical observations of the SF-nanobacteria cultures after heat treatment revealed that they had survived all the tested conditions including boiling at 100C for 30 minutes. Initially, reduction in the amount of viable SF-nanobacteria was observed with the higher temperatures, but after two weeks there was no difference in the test culture results as compared to the non-heated control.

Antibiotic Resistance of Nanobacteria

Figure 6:
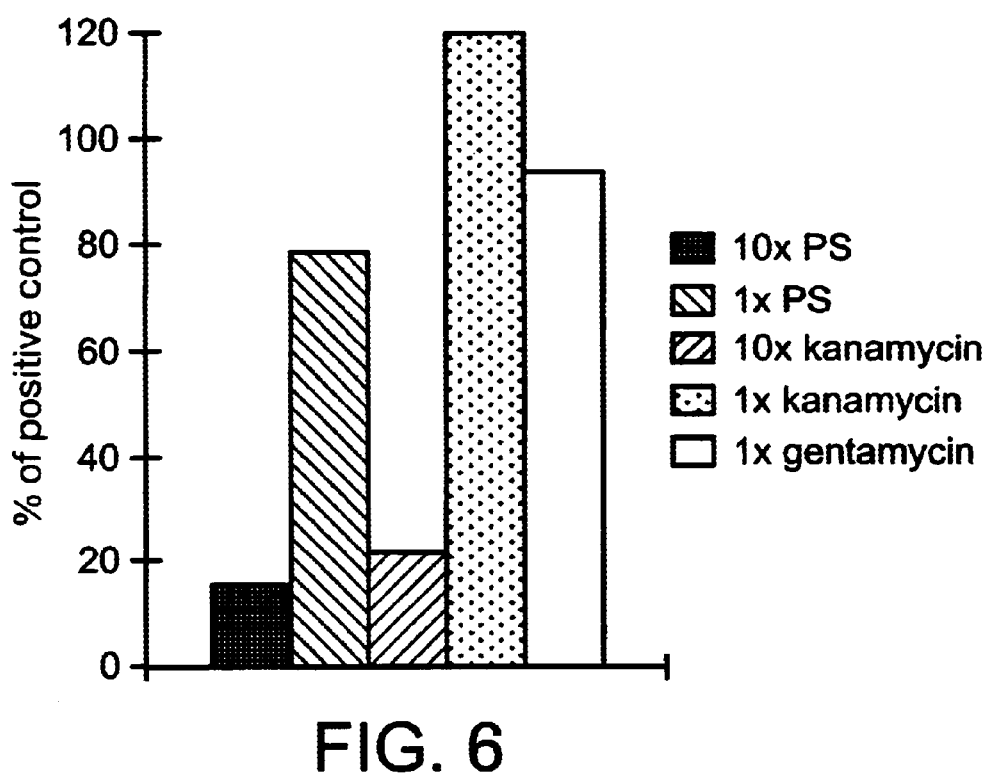
FIG. 6. Graphic presenting the effect of antibiotics on nanobacterial growth. The growth is compared to that of nanobacteria cultured without antibiotics. Doses of antibiotics ten times higher than recommended for use in cell culture were needed to prevent the growth of nanobacteria.
Figure 7A:
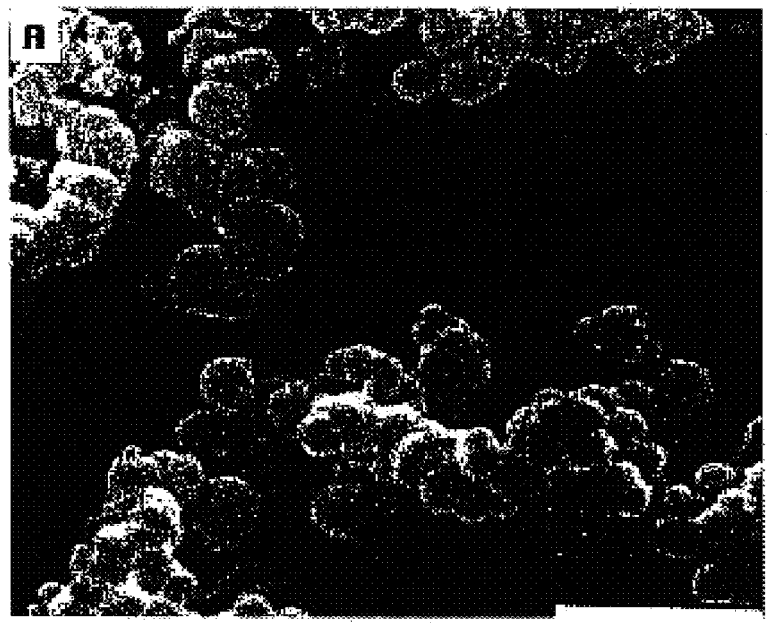
FIG. 7. SEM images of nanobacteria cultured with and without antibiotics for one month in medium containing 10% fetal bovine serum. Bars=1 $\mu$m. (A) Nanobacteria cultured without antibiotics. (B) Nanobacteria cultured with 100 $\mu$g/ml gentamycin. Arrows show changes in the morphology.
Figure 7B:
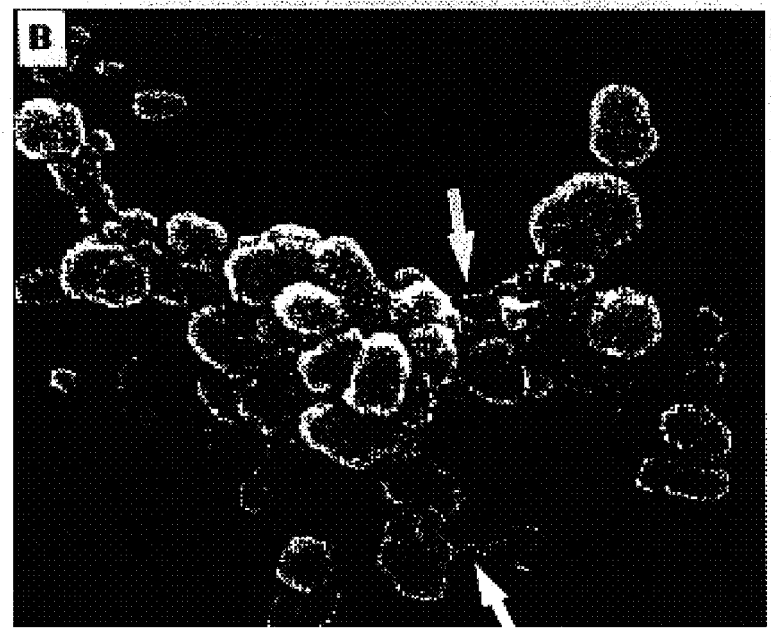

High resistance to the tested antibiotics was observed. Ten times higher concentrations than normally used in cell culture were needed to prevent the growth of nanobacteria. FIG. 6 shows the effect of antibiotics on growth of nanobacteria cultured with serum containing medium. Interestingly, at concentrations of antibiotics with no effect on growth, there was a profound effect in the morphology of nanobacteria as seen in SEM (FIGS. 7A and 7B). This suggests that nanobacteria have adaptive ways for protecting themselves for detrimental attacks, e.g., by secreting slimy layers.

Conclusions

Nanobacteria can tolerate harsh conditions extremely well. SF-nanobacteria were much more resistant than the nanobacteria cultured in serum containing medium. Extremes in pH, oxidizing agents, free chlorine, and chemicals affecting the proteins as well as irradiation, heat and drying have very little effect on SF-nanobacteria. This indicates that the mineral layer offers extra protection to the organism. Exceptional survival of nanobacteria has also been observed in association with human kidney stones. Viable nanobacteria were recovered from almost all kidney stones by demineralizing the stones with hydrochloric acid (see below).

An effective way to eradicate nanobacteria with disinfecting chemicals, should include a demineralization step. Apatite can be dissolved at low pH or by means of calcium chelators such as ethylenediaminetetraacetic acid (EDTA). A second step should be then included to kill the organism by another mechanism. Virkon, composed of peroxygen compounds, surfactant, organic acids and an inorganic buffer system, proved to be effective against nanobacteria most likely because of the acidity (1% solution in water has pH 2.6) combined with other disinfection mechanisms.

Doses of three megarads gamma irradiation are needed to ensure destruction of nanobacteria. Gamma irradiation is probably the best and most reliable method for killing nanobacteria. Drying at elevated temperatures or boiling for extended periods, can also be used in eradicating nanobacteria. Boiling for 30 minutes is effective against almost all living organisms, except some endospores, especially the spores of Bacillus stearothermophilus and hyperthermophilic archae having 90° C. or more as optimum temperature for growth. This treatment is also not enough to kill SF-nanobacteria. Importantly, normal autoclaving procedure (121° C. for 20 min) was also insufficient to eradicate nanobacteria.

Resistance of nanobacteria to the tested antibiotics was very high. Cell culture antibiotics used in this study are effective only in very high concentrations. A possible resistance mechanism is the production of a protective slime as revealed by SEM. Modificating the cell wall is a common strategy for many bacteria to acquire resistance to antibiotics. When a nanobacterium faces unfavorable conditions it starts to secrete polymers and form mineral upon them. The tested antibiotics were mainly aminoglycosides.

Observed resistance of serum nanobacteria shows that it is at least as resistant as Mycobacteria and Bacillus subtilis spores, which are the model organisms for disinfection resistance. The resistance of SF-nanobacteria is clearly superior to these.

The apatite mineral around the organism serves as a primary defense shield against various chemicals and irradiation. The survival of nanobacteria is clearly not only due to the mineral, because treatment with 1M hydrochloric acid could not kill nanobacteria, and remineralization could be observed later in the culture. A double defense with the apatite layer and impermeable membrane combined with a very slow metabolism is a likely explanation for the observed resistance of nanobacteria. The increased resistance of SF-nanobacteria is probably due to the extensive mineralization, slower metabolism and adherence to surfaces. Nanobacterial resistance mechanisms appear to be multiplicative: thus, nanobacteria having an apatite coat, impermeable cell wall, slow metabolism and possibly other still unknown mechanisms, becomes extremely resistant to most disinfecting methods.

EXAMPLE 3

Dental Pulp Stones Made by Nanobacteria

The purpose of the experiments conducted in this example was to investigate if nanobacteria participate in the dental pulp stone formation. The design of the study was to culture nanobacteria on a healthy tooth, without dental pulp stone, and compare the results with those obtained from a tooth having dental pulp stone. Mineral formations were observed under SEM. Additionally, an epidemiological screening was carried out on the possible correlation between dental pulp stone and kidney stone disease, and other bodily calcifications in 18 patients using a questionnaire.

Correlation Between Dental Pulp Stones and Other Stone Formation in the Body.

18 patients were randomly selected from a private dental practice in Turkey based upon their periodontal problems caused by severe pulp stone formation. Collected pulp stones were stored in PBS containing 0.05% $NaN_3$ at +4° C. The samples were demineralized in 1N HCl for 10 min at room temperature, neutralized with NaOH and potassium phosphate buffer, and immunostained by using anti-nanobacteria monoclonal antibodies. Treatment of the samples with 1N HCl did not effect the epitopes recognized by the monoclonal antibodies used in these experiments. Immunostaining revealed positive, small cocci at various concentrations in all samples. Specificity of the staining was further proven with negative staining results with three different monoclonal antibodies detecting nonrelevant antigens.

The results obtained from the patient questionnaire showed a high incidence of kidney stones and gallstones in both patients and their parents (Table 4).

TABLE 4

The presence of calcification and stone formation in the patients with dental pulp stones, and in their parents.

|  | Patients (9M + 9F) | Mothers | Fathers |
| --- | --- | --- | --- |
| Kidney stones | 5/18 (28%) | 3/18 (17%) | 6/18 (33%) |
| Urinary sand | 6/18 (33%) | 1/18 (6%) | 0/18 (0%) |
| Gallstones | 2/18 (11%) | 7/18 (39%) | 3/18 (17%) |
| Tissue calcifications | 1/18 (6%) | 5/18 (28%) | 1/18 (6%) |

There is an increase in calculus formation on teeth among the laboratory animals whenever common drinking water was given, which suggests that flora is transferred from one animal to an other. In addition, erythromycin strongly inhibits calculus formation, whereas chloramphenicol, and penicillin do not. This suggests that the organisms involved in calculus accumulation may be very specific. These findings provide a possible explanation to the results shown in Table 4, indicating high incidence for stone formation and calcification in the family members.

Nanobacteria Cause Dental Calculi Formation In Vitro

In SEM observations of a tooth with dental pulp stones (FIG. 8A), at high magnification, mineralized fibers, and numerous small globular bodies near them were observed (FIG. 8B). There were no calcospherules observed in the control tooth (FIGS. 8C and D).

Figure 9A:
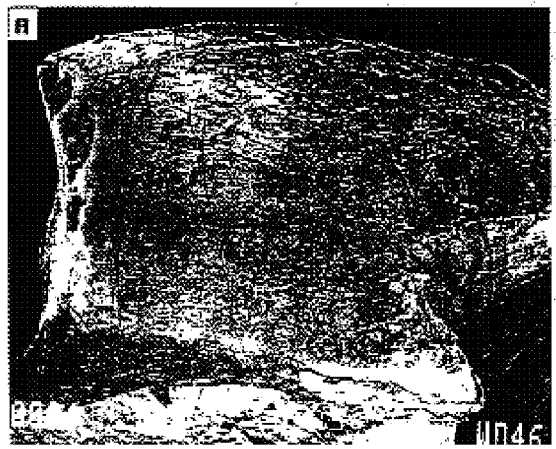
FIG. 9. SEM micrographs of the healthy tooth shown in FIGS. 8C and D after autoclaving, and incubating with SF-nanobacteria for one month in cell culture conditions. (A) General image showing the surface of the tooth, higher magnification to an area shown by the arrow is seen in (B). (C) Nanobacteria cultured for 3 months, and adhered to cell culture vessel; bar is 1 $\mu$m. (D) An area in the same tooth having voluminous pulp stone that appeared after SF-nanobacteria exposure for one month. (E) Higher magnification of the same area shown with big arrow in (D). Small arrows show the growth of SF-nanobacteria on the surface of calculi.
Figure 9C:
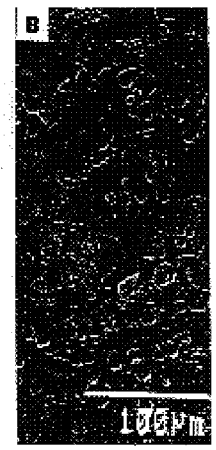
Figure 9B:
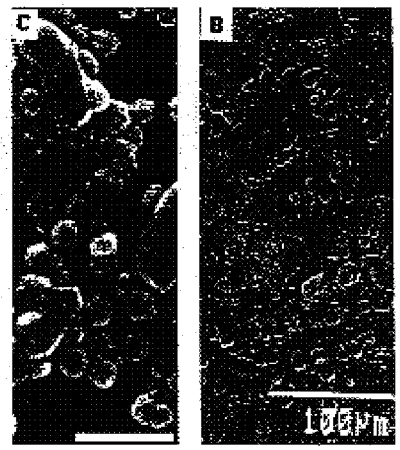
Figure 9D:
Figure 9E:

When the inventors exposed a healthy tooth to SF-nanobacteria culture for one month, SEM revealed voluminous mineral formation, resembling dental pulp stones, on the surface of the tooth (FIGS. 9A, B, D, and E).

The cavity-like structure indicated by the large arrows in FIG. 9 is a very typical structure for SF-nanobacteria (see above). It is suggested that different structural features correspond to various stages of mineralization of the pulp stones.

Figure 10A:
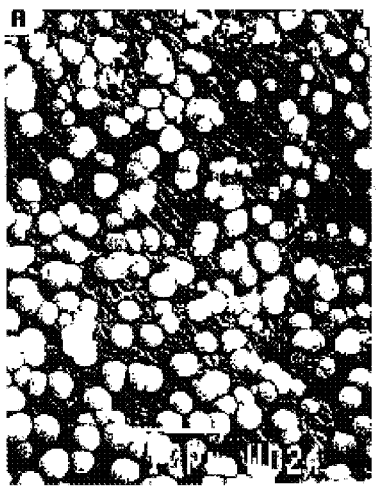
FIG. 10. SEM images of SF-nanobacteria growing on a piece of dolomite in the culture medium.
Figure 10B:
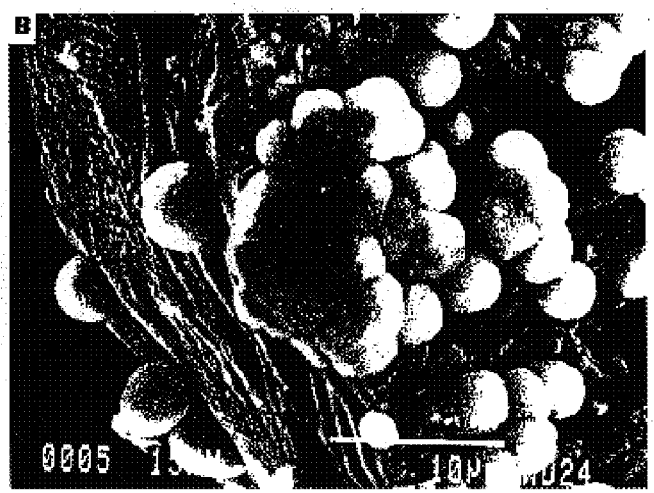

There are many ideas about the reason for dental calculi formation, e.g., diet, and age. Animal experiments have proven that addition of Ca and P to the diet increases the rate of dental stone formation. The present inventors have shown that Ca is very necessary element for production of apatite by nanobacteria. Addition of a sterilized dolomite piece to SF-nanobacteria culture increased their multiplication rate. SEM revealed adhered, multiplying SF-nanobacteria on the dolomite surface (FIG. 10).

Chemical Composition of Dental Pulp Stones

The features of crystal components of human dental calculi have been attributed to Ca/P molar ratio: i) calcified forms of microorganisms including cocci and rods with a Ca/P ratio close to 1.7, carbonated hydroxyapatite; ii) calcophoritic calcifications and dense calcifications with a Ca/P ratio close to 1.7, carbonated hydroxyapatite; iii) aggregated plates or clusters of platelets and fan-like aggregations with a Ca/P ratio close to 1.33, octacalcium phosphate; iv) cuboidal forms of varying sizes with a Ca/P ratio close to 1.4, whitlockite. The concentration of some other elements in dental pulp stones is much lower than Ca and P (0.88% F; 0.75% Na; 0.51% Mg). The other analyzed constituents (K, Cl, Mn, Zn, Fe) are present at trace concentrations.

Figure 11:
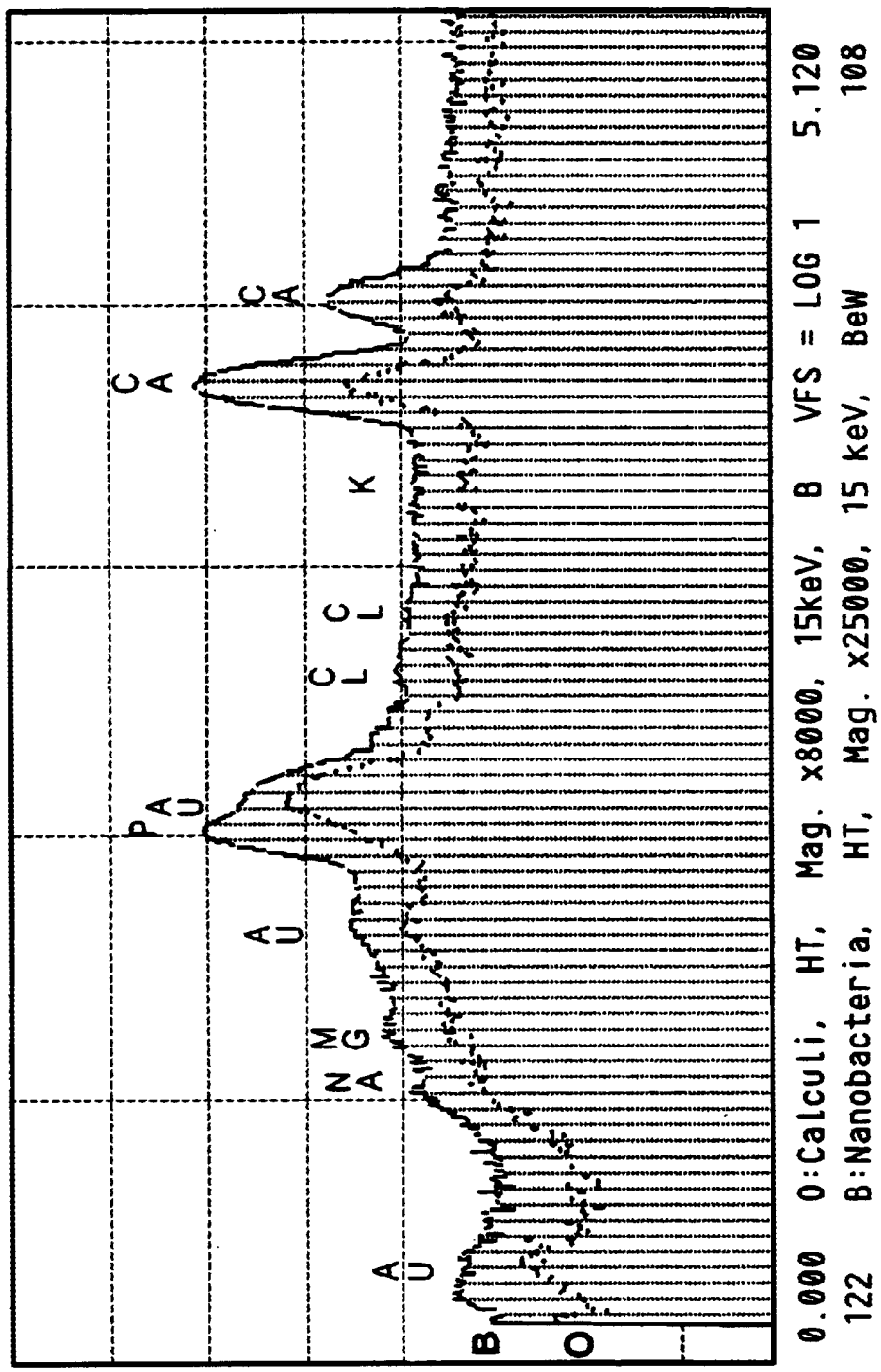
FIG. 11. Energy dispersive X-ray microanalysis of human dental calculi (O) and SF-nanobacteria (B).

In accordance with the aim of this study, to clarify the relationship between morphology, chemical composition of material in dental calculi, and nanobacteria, the EDX results were matched as seen in FIG. 11. Previously, the inventors identified with EDX and chemical analysis that all growth phases of nanobacteria produce biogenic apatite on their cell envelope. Fourier transform IR spectroscopy revealed the mineral as carbonate apatite.

Conclusion

These data indicates that dental pulp stones are associated with apatite forming nanobacteria.

EXAMPLE 4

Stone Formation and Calcification by Nanobacteria in Human Body

In these experiments, the inventors provide further evidence that nanobacteria can act as crystallization centers (nidi) for the formation of biogenic apatite structures in the mammalian body, and in environmental sources.

Calcification Caused by Nanobacteria in a Cell Culture Model

Figure 12A:
FIG. 12. Interaction of SF-nanobacteria with fibroblasts (3T6 cells). (A) SF-nanobacteria internalized by a fibroblast (arrow head shows the nanobacteria inside a vacuole), (B) higher magnification showing the needle-like apatite structure of the internalized SF-nanobacteria, (C) von Kossa staining result of the nanobacteria infected fibroblasts, and (D) negative control. Magnification in (C and D) is 270×. Arrow in (C) shows stained nanobacteria after staining with the von Kossa method which is a standard calcification detection method used in pathology.
Figure 12B:
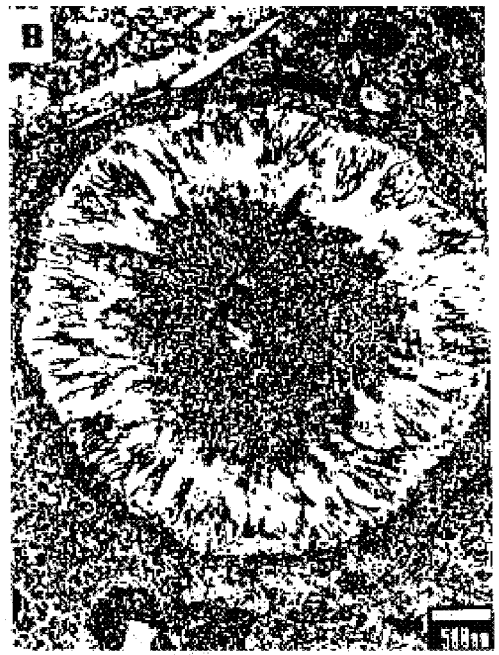
Figure 12C:
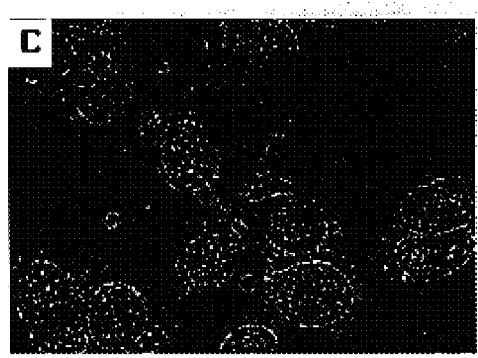
Figure 12D:
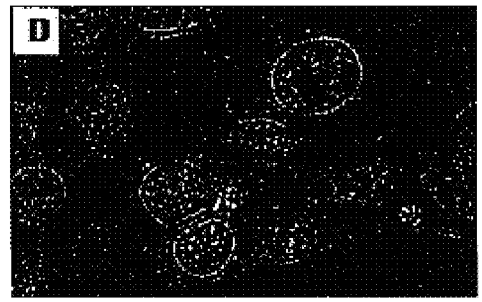

Nanobacteria are cytotoxic in vitro and in vivo. 3T6 fibroblastoid cells infected for 48 hours with nanobacteria (cultured in serum free condition, SF-nanobacteria), showed altered cell morphology due to internalized SF-nanobacteria (FIGS. 12A and B). von Kossa staining revealed intra- and extracellular calcification in the infected cells (FIG. 12C). Heavily infected cells showed nuclear abnormalities, e.g., macronucleus. There was no calcification and nuclear abnormalities in the control cells stained with the von Kossa method (FIG. 12D).

Nanobacteria and Kidney Stones

Figure 13A:
FIG. 13. TEM micrographs of a carbonate apatite human kidney stone and nanobacteria. (A) A kidney stone before demineralization, (B) SF-nanobacteria cultured for one month, (C) the same kidney stone after demineralization, (D) nanobacteria cultured in serum containing medium for 2 months. The kidney stone (C) was demineralized by incubating the smashed stone in 1N HCl for 10 min at room temperature, neutralized with NaOH and potassium phosphate buffer, and epon embedded. Both cultures of nanobacteria (B and D) adhered to the bottom of their culture vessels.
Figure 13B:
Figure 13C:
Figure 13D:
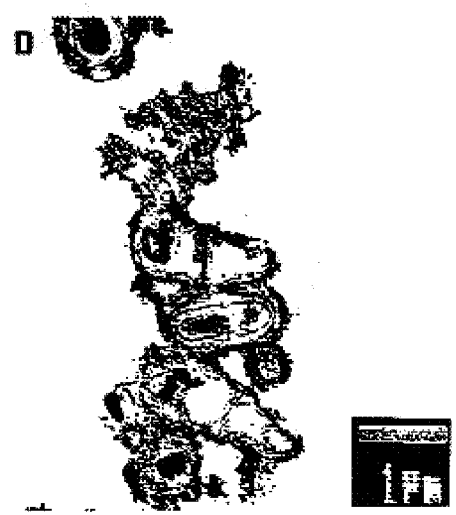

Urinary tract stone crystalline components are of five types: calcium oxalate, calcium phosphate, bacterial-related, purines or cystine. The majority of urinary stones are admixtures of two or more components, with the primary admixture being calcium oxalate with apatite. The viability and location of bacteria within infection stones (struvite [$MgNH_4PO_4 \cdot 6H_2O$] and/or carbonate apatite [$Ca_{10}(PO_4)_6CO_3$] stones) have been investigated. It was found that large numbers of bacterial impressions and bodies were existing in the interstices surrounded by crystals of apatite and struvite from the nuclei to the peripheral layers. The presence of bacterial colonies even in the nuclear portion of the stones suggests that bacteria participate in the initial stone formation, as well as in growth of infection stones. In the inventors' work, bacteria of similar size and morphology (FIGS. 13A and C) as nanobacteria (FIGS. 13B and D) were found with TEM in human kidney stones.

Figure 14A:
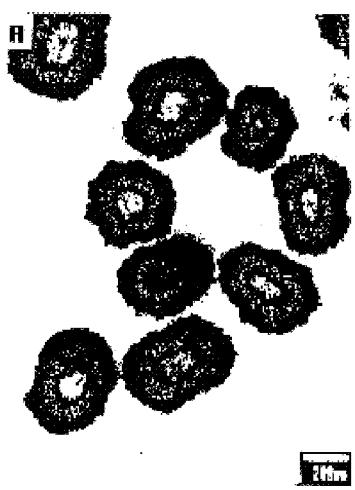
FIG. 14. TEM (A), and FITC images (B) of demineralized nanobacteria and immunofluorescence positivity in different kind of kidney stones (C–E). Kidney stones and nanobacteria were stained by using specific anti-nanobacteria monoclonal antibodies, after demineralization of the samples as described in FIG. 13. Thick arrows show immunofluorescence-positive individual coccoid particles. Immunopositivity on the surface of the small units composing the stone is shown with the small arrows. Magnifications: (B–D) 1600×; (E) 640×.
Figure 14B:
Figure 14C:
Figure 14D:
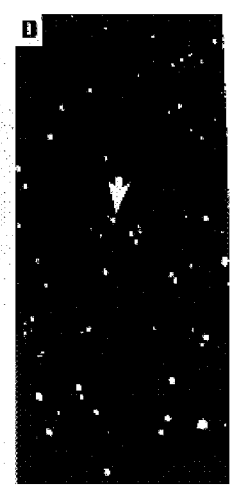
Figure 14E:
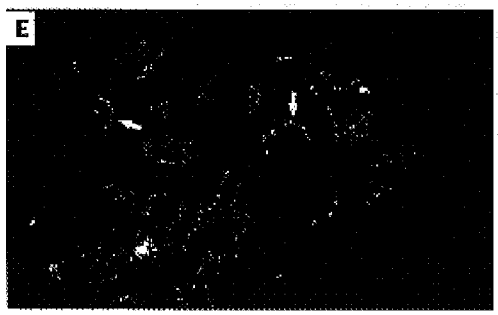

The present inventors screened 60 human kidney stones for nanobacteria using immunofluorescence staining and culture methods. Nanobacteria show a thick apatite envelope layer on their surface in TEM (FIG. 14A). Demineralization under harsh conditions (e.g., incubation with 1N HCl) did not affect their epitopes recognized by the monoclonal antibodies used in these experiments. Nanobacteria-specific monoclonal antibodies revealed positive, small cocci at various concentrations in all demineralized stone samples (FIGS. 14C–E) and nanobacteria (FIG. 14B). Different distribution patterns of nanobacteria were observed in the stones, e.g., central and/or peripheral location (FIG. 14E) in the small stone units, or random distribution (FIG. 14D). Specificity of the staining was further proven with negative staining results with four different monoclonal antibodies detecting nonrelevant antigens.

The demineralized, screened kidney stone samples were sterile-filtered through a 0.2 $\mu$m filter, and cultured under nanobacterial culture conditions for three weeks as described above. Gamma irradiated serum at 10% concentration was used as a culture supplement. In each experiment, only gamma irradiated serum culture was used as a negative control, and no growth was observed.

Figure 15A:
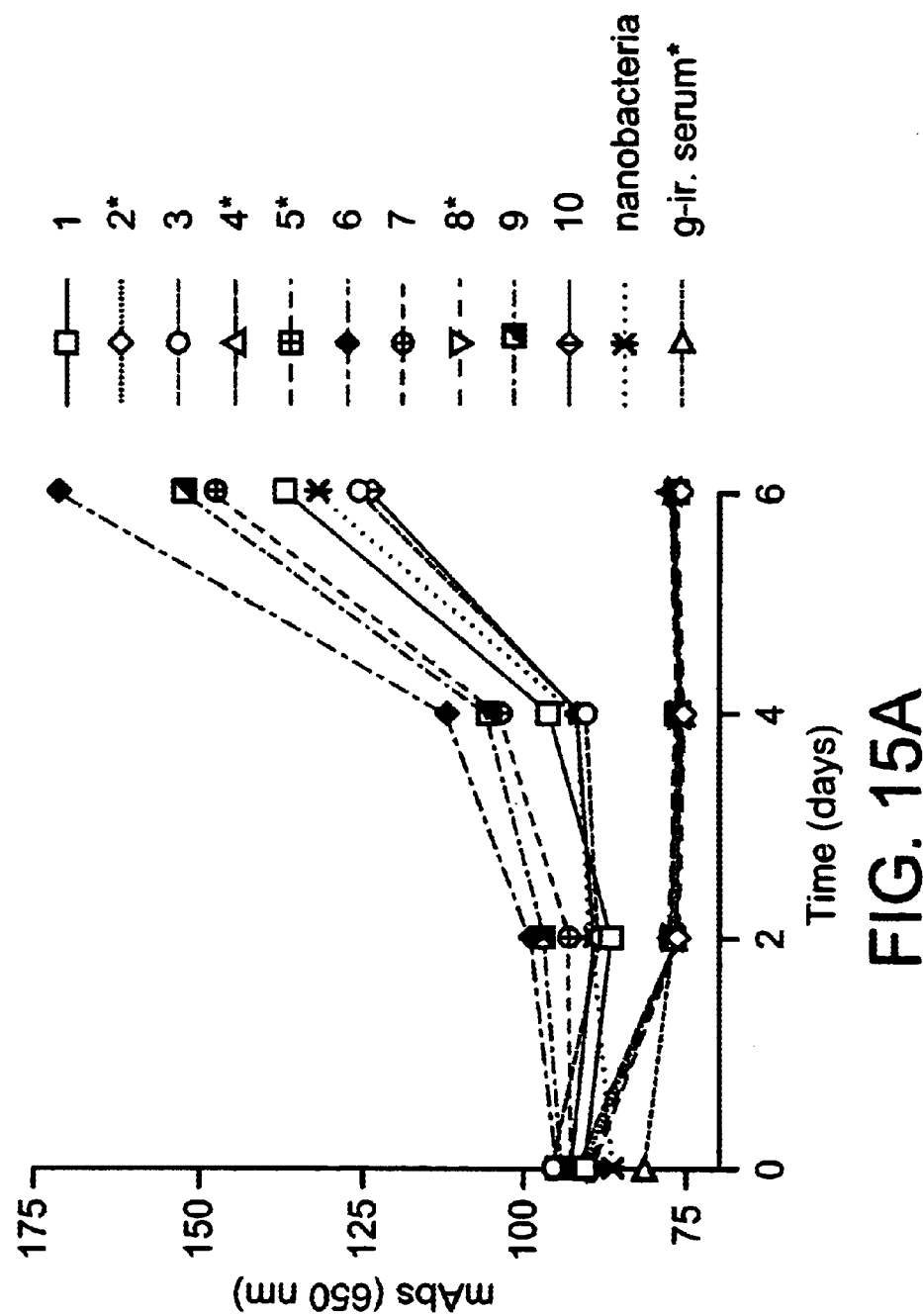
FIG. 15. Graphics showing the nanobacterial growth in the subculture of the demineralized, neutralized and sterile-filtered 20 different human kidney stones, and nanobacteria. * Indicates no growth in the first 6 days.
Figure 15B:
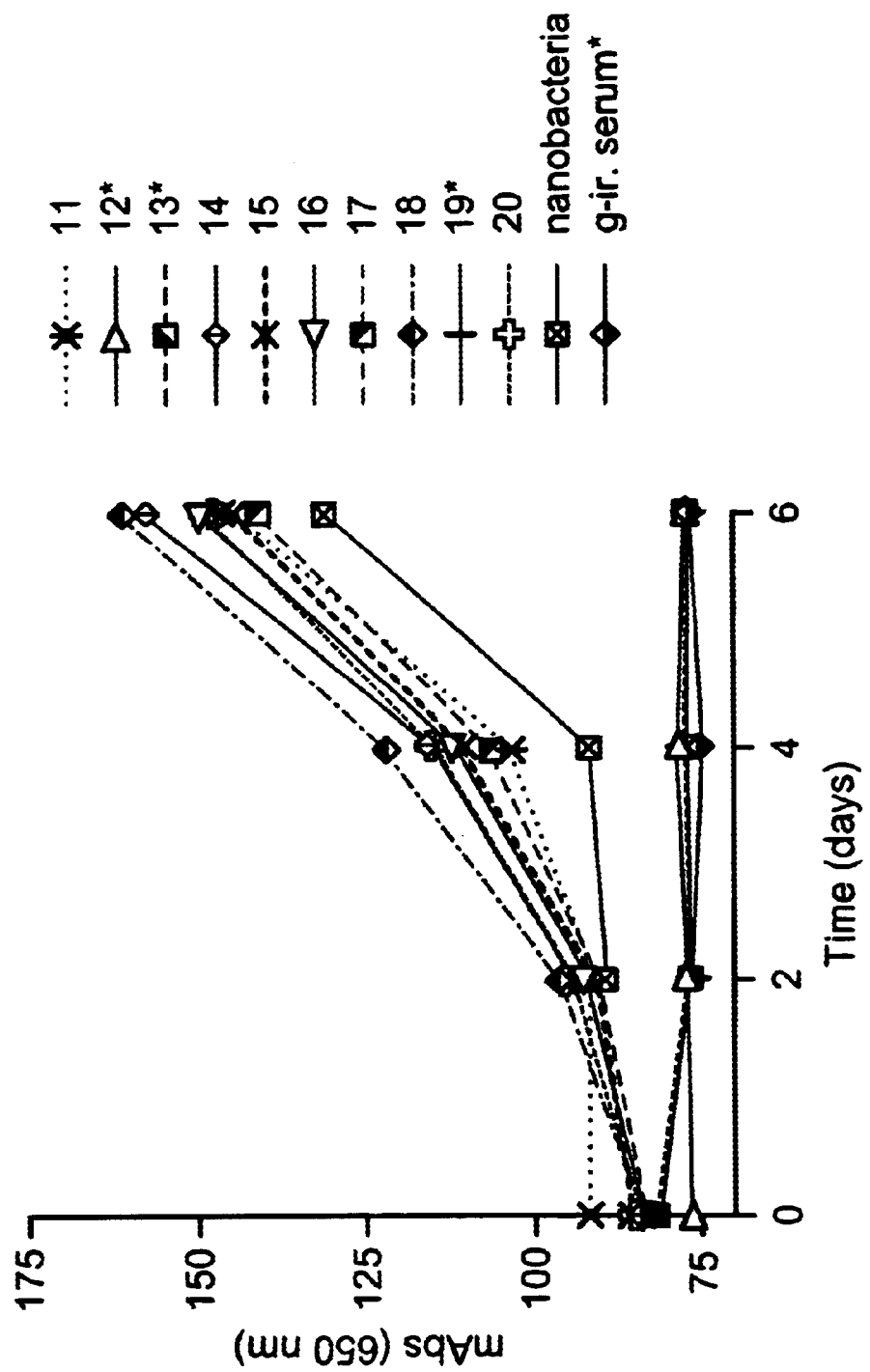

Interestingly, the present inventors observed nanobacterial growth in 90% of the stone samples despite the harsh demineralization step. In addition, the stones had been stored at room temperature for more than one month before screening. Demineralized control nanobacteria, the positive controls, multiplied well (FIGS. 15A and B). Nucleic acid staining by using Hoechst (#33258) stain proved no other kind of bacterial growth was present in the cultures. For further proof, 3T6 cells were infected with the nanobacteria cultured from stone samples, and stained with anti-nanobacteria monoclonal antibodies. Five different kind of nanobacteria-cell interaction was observed (data not shown).

Conclusions

Nanobacteria are novel emerging pathogens and may be related to small mineral forming bacteria found in sedimentary rocks, linking medicine to geology. They produce biogenic apatite in vitro and also seem to do so in vivo. Since apatite is considered to be the main nidus initiating the formation of most kidney stones, nanobacteria seem to be excellent candidates for triggering this process. Nanobacteria injected to blood circulation of laboratory animals were shown to penetrate through kidney cells and pass into urine. In urine, apatite formation by nanobacteria is further increased. Other minerals may thereafter bind onto this nidus.

EXAMPLE 5

Treatment of a Human Patient Infected With Nanobacteria.

The present inventors have now treated one 35-year-old Finnish female suffering from chronic fatigue syndrome for nanobacterial infection. The patient was nanobacteria-positive in three urine and serum samples collected before tetracycline therapy was commenced. She received 500 mg tetracycline HCl 4 times per day for one month, followed by 500 mg twice a day for 5 months. The patient was nanobacteria negative after one month therapy. Her condition was improved simultaneously and she has remained negative in monthly samples.

EXAMPLE 6

Antibiotic Susceptibility of Nanobacteria

Antibiotic sensitivity tests were carried out by measuring Minimal Inhibition Concentration (MIC), a common practice in clinical microbiology.

Methods

The tests were performed in 96-well plates. DMEM (commercial cell culture medium) containing 10% gamma-irradiated fetal bovine serum (FBS)(dose about 3 Mrads; this treatment inactivates nanobacteria in the serum so that the basic medium is sterile) was used as the basic culture medium. These components are commercially available, e.g., from Gibco. The antibiotic stock solutions were sterile filtered through 0.2 micrometer filters. The stock solutions were then serially diluted (into the basal culture medium) to provide a final starting concentration of 0.5 mg/ml and 1:2 dilutions therefrom, unless otherwise specified. For each antibiotic three parallel tests were performed using all the antibiotic dilutions and, additionally, positive and negative control experiments. Positive controls had nanobacteria with no antibiotic addition, while negative controls had only the basic medium. Nanobacteria were cultured from FBS, human serum from a patient having Polycystic Kidney Disease (PKD), and from human kidney stones as described in our earlier work (Kajander and Ciftcioglu, PNAS 95:8274–8279, 1998). 100 μl of dilutions of the nanobacteria inoculum were added to all wells except the negative controls. The plates were incubated at mammalian cell culture conditions (37° Celsius, 5% carbon dioxide, 95% humid air). The absorbance values at 650 nm were recorded by using an ELISA reader at the start, and at 4, 8, 12, 14 days. Final MIC values (50% and 90% inhibition) were calculated at the 12 day time point. Calculations were based on absorbance curves where absorbance was plotted against concentration of the antibiotic.

Results

The results of these experiments are summarized in Table 5.

TABLE 5

Summary of MIC 50 and MIC 90 values for selected antibiotics (mg/l):

| Compounds | MIC 50 | MIC 90 |
|---|---|---|
| Trimethoprim-Sulphamethaxazole | 15 | >500 |
| Trimethoprim | 0.7 | 5 |
| Tetracycline | 0.3 | 1.3 |
| Doxycyclin | 50 | 80 |
| Nitrofurantoin | 0.6 | 1.5 |
| Gentamycin | 60 | 250 |
| Neomycin | 16 | 30 |
| Kanamycin | 50 | 200 |
| Vancomycin | 130 | 250 |
| Ampicillin | 500 | |
| Cefuroxim | >500 | |
| Pyrazinamide | >500 | |
| Ethambutol | >500 | |
| Metronidasole | >500 | |
| Ciprofloxacine | >500 | |
| Rifampicin | >500 | |
| Clarithromycin | >500 | |
| Clindamycin | >500 | |
| Spectinomycin | >500 | |
| Streptomycin | >500 | |
| Cephalothin | >500 | |
| Erythromycin | >500 | |
| Lincomycin | >500 | |
| Chloramphenicol | >500 | |
| Penicillin | >500 | |
| Polymyxin B | >500 | |

As can been seen from the results presented in Table 5, the trimethoprim-sulphamethaxazole combination was not as effective as trimethoprim alone (FIG. 24). This was somewhat surprising in view of the fact that this combination is widely used in the treatment of urinary tract infections. Trimethoprim is highly effective but was only bacteriostatic in the in vitro test (FIG. 16). Trimethoprim is a very potential antinanobacteria drug for human and animal therapy.

Tetracycline is highly effective and was bactericidal in the in vitro test (FIGS. 17, 25). Kidney stone patients treated with 4×500 mg/day initially had nanobacteria-positive urine culture results, but began to have negative urine cultures during the treatment. This indicates that tetracycline treatment can be effective in human and animal treatments for nanobacteria eradication. As stated previously, tetracycline is bound and concentrated to the mineral surface of nanobacteria. This may explain why tetracycline has bactericidal effect on nanobacteria. This bactericidal effect is unique to nanobacteria: other bacteria show only bacteriostatic effect. Tetracyclines are thus potential drugs for eliminating nanobacteria from cell cultures and biological products. Because the drug is bound to nanobacteria, even short exposure periods have substantial antinanobacterial effect.

Nitrofurantoin is highly effective but was bacteriostatic in vitro (FIG. 18). This compound is used for urinary tract infections only because of its rapid elimination into urine. In addition to human and animal antinanobacterial therapies, nitrofurantoin can be useful in eliminating or reducing the number of nanobacteria in cell cultures and biological fluids and products.

Doxycycline, which is also a tetracycline compound, was effective on inhibiting nanobacterial growth (FIG. 19). This compound was not stable under the test conditions. MIC values calculated from the 8 day results indicated effectiveness at around 1 mg per liter. Thus doxycycline would also be a good candidate for the human and animal therapies. It should be noted that tetracyclines have been used in the treatment of pathological calcifications and autoimmune diseases with often remarkably good results.

The aminoglycoside antibiotics gentamycin, neomycin, kanamycin (FIGS. 20–22), and streptomycin all show antinanobacterial bacteriostatic effects at high antibiotic concentrations. Such concentrations are present in local drug forms, such as skin cream, ointment, plasters or washing solutions and in ear and eye drops. Their antinanobacterial effect offers a novel explanation for the known efficacy of gentamycin and streptomycin in the treatment of inner ear problems involving pathological calcification, such as Menier's disease.

Vancomycin is an effective bacteriostat against nanobacteria at relatively high concentrations (FIG. 23). Such concentrations can be present in local therapies with this drug. Vancomycin is not absorbed from the gastrointestinal tract or other mucosal surfaces, but can be used to treat mucosal bacterial infestation. Thus vancomycin can be effective in eradication of gastrointestinal nanobacteria or in other local applications.

Ampicillin is a wide-spectrum penicillin group antibiotic. Ampicillin shows a weak bacteriostatic effect on nanobacteria. Since ampicillin and related drugs are administered at very high doses and are concentrated into urine at levels exceeding the observed MIC values, they can be useful in the treatment of urinary tract nanobacterial infection.

Other tested antibiotics were found to have MIC values exceeding 500 mg per liter. These antibiotics are thus unlikely to be effective in eradication of nanobacteria when used in monodrug therapy, although they may be effectively employed in conjunction with other antibiotics in a multidrug treatment regimen.

As shown in Table 2, bisphosphonates, as exemplified here by chlodronate and ethidronate, are extremely effective antinanobacterial agents that exert a bacteriocidic effect on nanobacteria at concentrations much smaller than those found in patients treated with the drug. This is a novel finding in microbiology, since these drugs have not been used for antibacterial therapies. These drugs are in medical use because of their effects on bone resorption in cancer or osteoporosis. Recent publications indicate that bisphosphonates can reduce pathological calcification, an opposite reaction to their accepted use, in atherosclerosis. Atherosclerosis involves calcification, the nature of which has not been understood. We suggest that atherosclerosis may be partly an infectious disease that involves nanobacteria as copathogens with *Chlamydia pneumoniae* or other agents, including local viral infections.

TABLE 6

Summary of MIC 50 and MIC 90 values for selected Ca chelators and other compounds:

| Compounds | MIC 50 | MIC 90 |
|---|---|---|
| Chlodronate | 0.1 mg/l | 0.5 mg/l |
| Ethidronate | 0.1 mg/l | 0.5 mg/l |
| Citrate | 0.2 mM | 1 mM |
| EDTA | 0.3 mM | 2.5 mM |
| Vitamin K (Menadion) | 2 mg/l | |
| Vitamin D | >0.025 mM | |
| Acetylsalicylic acid | 0.5 g/l | |

Bisphosphonates can be used for the elimination of nanobacteria in cell cultures, biological fluids and products. They are concentrated on the nanobacterial apatite and kill the nanobacteria relatively rapidly, even after a single exposure. Thus they can be useful in industrial nanobacteria elimination, e.g., from FBS. FBS or other sera can be exposed to low levels, e.g. micrograms to grams per liter, of a bisphosphonate that will inactivate nanobacteria and prevent their multiplication when the serum is used in industrial or research purposes (e.g., in tissue or cell culture). A similar approach can be used to treat human blood and blood derived products, vaccines, cell culture products and biotechnological products. Treatment time can be from minutes to days and treatment temperature from 0–100° Celsius. Treatment can be carried out in solutions having pH 3–10. The drug is harmless to humans or animals at low levels. If necessary, the drug can be removed from the serum or product after the exposure, e.g., by using dialysis, or reduced to low levels by absorption on calcium phosphate mineral surfaces (apatite and other calcium minerals will do it), e.g., by using apatite filters or particles. Because bisphosphonates are excreted and highly concentrated in urine, they are highly potent drugs to treat nanobacterial diseases like kidney stones.

Citrate is an effective antinanobacterial agent at concentrations that can be reach by oral or intravenous or local treatments in humans or animals. Citrate chelates calcium. Calcium is a key element for nonobacterial cell wall integrity. Similarly other short organic acids are weak calcium chelators and can be useful in nanobacterial eradication. Such acids include lactic acid, acetic acid and natural products containing acids, e.g., cranberry juice. The later has been used to treat urinary tract infections. However, the mechanism of action against nanobacteria appears to be a weakening of apatite cell wall, whereas cranberry juice is thought to prevent adhesion of common bacteria in the urinary tract. Similarly trials with citrate for treatment of kidney stones have been made because citrate lowers free calcium levels. However, the present inventors have discovered that these acids exert antinanobacterial effect. Most importantly, citrate is much more effective than strong acids, e.g., HCl, in killing nanobacteria. Other short chain organic acids have been tested later: acetic acid, lactic acid, and ascorbic acid all showed inhibitory effect on nanobacteria in culture tests. Their MIC50 values were 10–50 mM indicating potential for antinanobacterial therapy.

EDTA and EGTA are calcium chelators that exert antinanobacterial effects. They can be used in patient treatment as exemplified by the use in divalent cation, e.g., lead, poisoning. Furthermore, such agents can be used in drug and biotechnology preparations to prevent nanobacteria growth or inactive them.

Vitamin K is toxic to nanobacteria at concentrations that are not harmful to mammalian cells. The compound is adsorbed by apatite and thus is concentrated by nanobacteria. Vitamin K may be used as an anti-nanobacterial agent in the treatment of serum or biotechnological products. After treatment excessive amounts can removed by extraction with organic solvents or lipophilic filters, hydrophobic chromatography or affinity chromatographic techniques using affinity matrixes binding vitamin K or similar methods.

Vitamin D modifies calcium metabolism and has a very weak inhibitory effect on nanobacteria.

Acetylsalicylic acid is structurally rather similar to para-amino salicylic acid, which is used as antituberculosis agent. These compounds affect the cell wall or other targets in nanobacteria. The effect is weak but such agents can be used at high concentrations which makes them as potential drugs against nanobacteria. Imporantly, para-aminosalicylic acid used in tuberculosis treatment was found to have similar effect: its MIC value wasa identical with acetylsalicylic acid. This may apply for other anti-inflammatory drugs having a short-chain acid moiety.

Dental pulp stones contain apatite mineral in a biomatrix. We have shown that nanobacteria can be found from human dental pulp stones and that nanobacteria grow on human teeth producing identical stones than the natural dental pulp stones. Fluoride was found to inhibit nanobacterial stone formation on human teeth under in vitro culture model using the fluoride concentrations typically present in toothpastes.

Nanobacteria also absorb some heavy metals. Nanobacteria can be stained well with silver or copper compounds. Moreover, silver and copper ions added to nanobacterial culture media at submillimolar levels prevented nanobacterial growth. Silver and copper parts or platings on surfaces, such as catheters or stents, can provide an antinanobacterial effect by preventing nanobacterial biofilm formation. In in vitro tests nanobacteria avidly formed biofilm on two different commercial stents made of a plastic type of material. This biofilm formation was prevented by the addition of silver or copper salts to the culture medium.

Drug Combinations

The most potent antibiotic, tetracycline, was tested in combination with the most potent nonantibiotic drug, ethidronate. It was found that combinations of these drugs, at concentrations that are ineffective when administered alone, produced a marked antinanobacterial effect. The MIC 90 value was about 0.01 mg per liter for the combination, whereas individual compounds had MIC values much higher. Thus, a synergistic effect was present. Such an effect may be useful in designing drug combinations for antinanobacterial effect. Specifically, therapy with combination of an antibiotic together with a bisphosphonate, a calcium chelators, a weak acid (such as citric, lactic, or acetic acid), or an anti-inflammatory acidic drug (such as aspirin) is useful in the treatment of nanobacterial infection, especially pathological calcification and stones, such as kidney stones and salivary stones. For treatment of nanobacteria in dental pulp stones fluoride may be included into the combination.

The drugs can be administered in the form of a toothpaste, mouth wash or dental adhesive coating.

EXAMPLE 6

Susceptibility of Nanobacteria to Sonication

Eradication of nanobacteria in solutions was tested also by using sonication with B.Braun Labsonic 2000 sonicator. The sample, nanobacteria-contaminated commercial FBS (fetal bovine serum), was subjected to sonication at full power in 100 ml portions using round conical container (175 ml nominal volume, Nalgene Cat. No 3143). The procedure followed the sonicator manufacture's instructions. The sound tip was selected to produce high power sonication, and was introduced 1 cm above the bottom of the tube. Ultrasound was given at 1 min pulses with 1 min pauses on ice bath to prevent heating of the sample. The real sonication times were 0, 1, 2, 3, 5 and 10 min. Thereafter, the samples were subjected to standard nanobacteria culture. Samples from 5 and 10 min sonication revealed no culturable organisms.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method for disinfecting an article contaminated with nanobacteria, comprising exposing the nanobacteria to an effective amount of disinfectant for a sufficient amount of time,
   wherein the disinfectant is selected from the group consisting of
   a 1% mixture (by weight) of a solution of 50% (by weight) potassium persulfate, 15% (by weight) sodium alkyl benzene sulphonate, and 5% (by weight) sulfaminoic acid in distilled water,
   a 3% mixture (by weight) of 4.5% formaldehyde (by weight), 6.8% glyoxal (by weight), 1.5% glyoxylic acid (by weight), and 6% dimethyllaurylbenzyl-ammoniium chloride (by weight), and
   a low molecular weight organic acid that binds or chelates calcium.

2. The method according to claim 1, wherein the low molecular weight organic acid is selected from the group consisting of citric acid, acetic acid, lactic acid, ascorbic acid, and salicylic acid, and its acetyl and aminoacetyl derivatives.

3. A method for disinfecting an article contaminated with nanobacteria comprising demineralizing the nanobacteria by exposing the article to a sufficiently low pH or a calcium chelator an effective amount of calcium chelator for a sufficient amount of time, and then exposing the article to an effective amount of a disinfectant for a sufficient amount of time,
   wherein the disinfectant is hydrochloric acid; and
   wherein the article is autoclaved at a temperature of at least 121° C. for at least 20 minutes.

4. A method for disinfecting an article contaminated with nanobacteria comprising demineralizing the nanobacteria, and then exposing the article to an effective amount of a disinfectant for a sufficient amount of time, wherein demineralization is accomplished by exposing the article to an effective amount of a calcium chelator for a sufficient amount of time;
   wherein the calcium chelator is EDTA or a bisphosphonate;
   and wherein the disinfectant is selected from the group consisting of hydrochloric acid; guanidium hydrochloride; a solution of 50% (by weight) potassium persulfate, 15% (by weight) sodium alkyl benzene sulphonate, and 5% (by weight) sulphamic acid; and a solution of 4.5% (by weight) formaldehyde, 6.8% (by weight) glyoxal, 1.5% (by weight) glyoxylic acid, and 6% (by weight) dimethyllaurylbenzyl-ammonium chloride.

5. The method according to claim 4, wherein the calcium chelator is EDTA.

6. A method for disinfecting an article contaminated with nanobacteria comprising demineralizing the nanobacteria, and then exposing the article to an effective amount of a disinfectant for a sufficient amount of time, wherein the disinfectant is selected from the group consisting of hydrochloric acid;
   guanidium-hydrochloride;
   a solution of 50% (by weight) potassium persulfate, 15% (by weight) sodium alkyl benzene sulphonate, and 5% (by weight) sulphamic acid;
   a solution of 4.5% (by weight) formaldehyde, 6.8% (by weight) glyoxal, 1.5% (by weight) glyoxylic acid, and 6% (by weight) dimethyllaurylbenzyl-ammonium chloride;
   and mixtures thereof.

7. A method for disinfecting an article contaminated with nanobacteria comprising demineralizing the nanobacteria, and then exposing the article to an effective amount of a disinfectant for a sufficient amount of time, wherein the disinfectant is selected from the group consisting of
   guanidium-hydrochloride ( at least a 3M solution);
   a solution of 50% (by weight) potassium persulfate, 15% (by weight) sodium alkyl benzene sulphonate, and 5% (by weight) sulphamic acid;
   a solution of 4.5% (by weight) formaldehyde, 6.8% by weight) glyoxal, 1.5% (by weight) glyoxylic acid, and 6% (by weight) dimethyllaurylbenzyl-ammomium chloride; and mixtures thereof.

8. A method for disinfecting an article contaminated with nanobacteria comprising demineralizing the nanobacteria by exposing the article to a sufficiently low pH or an effective amount of a calcium chelator for a sufficient amount of time, and then autoclaving the article at a temperature of at least 121° C. for at least 20 minutes.

9. A method for disinfecting an article contaminated with nanobacteria comprising by demineralizing the nanobacteria by exposing the article to a sufficiently low pH or an effective amount of a calcium chelator for a sufficient amount of time, and then exposing the article to an effective amount of a disinfectant for a sufficient amount of time,
   wherein the article is exposed to ultraviolet radiation, by exposing the article to a UV-C lamp of at least 15 W at a distance of 60 cm or less for at least 1 hour, or with any UV-C source delivering a similar or higher radiation dose; and
   wherein the disinfectant is selected from the group consisting of: hydrochloric acid; guanidium-hydrochloride; a solution of 50% (by weight) potassium persulfate, 15% (by weight) sodium alkyl benzene sulphonate, and 5% (by weight) sulphamic acid; and a solution of 4.5% (by weight) formaldehyde; 6.8% (by weight) glyoxal, 1.5% (by weight) glyoxylic acid, and 6% (by weight) dimethyllaurylbenzyl-ammonium chloride.

10. A method for disinfecting an article contaminated with nanobacteria comprising demineralizing the nanobacteria by exposing the article to a sufficiently low pH or an effective amount of a calcium chelator for a sufficient amount of time, and then exposing the article to ultraviolet radiation, by exposing the article to a UV-C lamp of at least 15 W at a distance of 60 cm or less for at least 1 hour.

11. A method for disinfecting an article contaminated with nanobacteria comprising demineralizing the nanobacteria by exposing the article to a sufficiently low pH or an effective amount of a calcium chelator for a sufficient amount of time, and then heating the article for at least 15 minutes, at a temperature of at least 60° C.

12. A method for disinfecting an article contaminated with nanobacteria comprising demineralizing the nanobacteria by exposing the article to a sufficiently low pH or an effective amount of a calcium chelator for a sufficient amount of time, and then heating the article for at least 30 minutes at a temperature of at least 100° C.

13. A method for inhibiting or treating the development of calcifications in vivo in a patient in need of such inhibition or treatment, comprising administering an antibiotic to the patient in an amount sufficient to inhibit the growth of nanobacteria;

wherein the antibiotic is selected from the group consisting of β-lactam antibiotics, aminoglycoside antibiotics, tetracycline antibiotics, trimethoprim antibiotics, nitrofurantoin antibiotics and pharmaceutically acceptable salts thereof, and mixtures thereof.

14. The method according to claim 13, wherein the β-lactam antibiotics are selected from the group consisting of penicillin, phenethicillin, ampicillin, azlocillin, bacmpicillin, carbenicillin, cylclacillin, mezlocillin, piperacillin, epicillin, hetacillin, cloxacillin, dicloxacillin, methicillin, nafcillin, oxacillin, and pharmaceutically acceptable salts thereof.

15. The method according to claim 13, wherein the aminoglycoside antibiotics are selected from the group consisting of streptomycin, kanamycin, gentamycin, amikacin, neomycin, pardomycin, tobramycin, viomycin, and pharmaceutically acceptable salts thereof.

16. The method according to claim 13, wherein the tetracycline antibiotics are selected from the group consisting of tetracycline, chlortetracycline, demeclocycline, doxycycline, methacycline, oxytetracycline, rolitetracycline, minocycline, sancycline, and pharmaceutically acceptable salts thereof.

17. The method according to claim 13, wherein the antibiotic is coadministered with a calcium chelator or sequestering agent, wherein the calcium chelator or sequestering agent is EDTA or a citrate compound.

18. A method for inhibiting or treating the development of calcifications in vivo in a patient in need of such inhibition or treatment, comprising administering a bisphosphonate to the patient in an amount sufficient to inhibit the growth of nanobacteria, wherein the bisphosphonate is selected from the group consisting of alendronic acid, etidronic acid, clodronic acid, oxidronic acid, and pharmaceutically acceptable salts thereof; and wherein the bisphosphonates are administered at a dose of approximately 0.001–100 mg/kg/day.

19. The method according to claim 18, wherein the bisphosphonates are administered at a dose of approximately 5–20 mg/kg/day.

20. The method according to claim 18, wherein the bisphosphonates are coadministered with an antibiotic.

21. The method according to claim 20, wherein the antibiotic is a tetracycline antibiotic, selected from the group consisting of tetracycline, chlortetracycline, demeclocycline, doxycycline, methacycline, oxytetracycline, rolitetracycline, minocycline, sancycline, and pharmaceutically acceptable salts thereof.

22. A method for inhibiting the development of kidney stones in a patient that has previously suffered from kidney stones, comprising administering an antibiotic to the patient in an amount effective to inhibit the growth of nanobacteria, wherein the antibiotic is selected from the group consisting of β-lactam antibiotics, aminoglycoside antibiotics, tetracycline antibiotics, trimethoprim antibiotics, nitrofurantoin antibiotics, pharmaceutically acceptable salts thereof and mixtures thereof.

* * * * *